(12) United States Patent
Hahn et al.

(10) Patent No.: US 8,247,493 B2
(45) Date of Patent: Aug. 21, 2012

(54) LONG ACTING FORMULATION OF BIOPHARMACEUTICAL

(75) Inventors: Sei-Kwang Hahn, Kyungsangbukdo (KR); Hyun-Gu Kang, Kyungsangbukdo (KR); Sung-Ho Ryu, Kyungsangbuk-do (KR); Jung-Kyu Park, Daejeon (KR); Eun-Ju Oh, Busan (KR)

(73) Assignees: Postech Academy-Industry Foundation, Pohang (KR); Posco, Pohang-shi (KR)

( * ) Notice: Subject to any disclaimer, the term of this patent is extended or adjusted under 35 U.S.C. 154(b) by 579 days.

(21) Appl. No.: 12/422,950

(22) Filed: Apr. 13, 2009

(65) Prior Publication Data
US 2011/0111477 A9 May 12, 2011

Related U.S. Application Data

(63) Continuation of application No. PCT/KR2007/005179, filed on Oct. 22, 2007.

(51) Int. Cl.
*A61K 47/48* (2006.01)

(52) U.S. Cl. .................................................. 525/54.2
(58) Field of Classification Search .................. 525/54.2
See application file for complete search history.

(56) References Cited

U.S. PATENT DOCUMENTS
2004/0019157 A1  1/2004  Won
2004/0147687 A1  7/2004  Rosen et al.

FOREIGN PATENT DOCUMENTS
WO    WO 2005/084412 A2    7/2005

OTHER PUBLICATIONS

Gaertner, et al., "Site-Specific Attachment of Functionalized Poly-(ethylene glycol) to the Amino Terminus of Proteins," Bioconjugate Chemistry, 7(1):38-44, 1996.
Kim et al., "Peptide Dendrimers from Natural Amino Acids," Chemistry-A European Journal, 5(7):2133-2138, 1999.

*Primary Examiner* — Edward Cain
(74) *Attorney, Agent, or Firm* — Joseph Hyosuk Kim; JHK Law

(57) ABSTRACT

The invention relates to a long-acting formulation of biopharmaceutical, more specifically an aptamer therapeutics. A branched PEGylated aptamer or a hyaluronic acid (HA) derivative of which degradation in vivo is regulated is linked by the bioconjugation with biopharmaceutical to produce the long-action formulation.

2 Claims, 11 Drawing Sheets

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Anti-thrombin DNA aptamers sequence

<400> SEQUENCE: 1

```
ggttggtgtg gttgg                                         15

<210> SEQ ID NO 2
<211> LENGTH: 23
<212> TYPE: DNA
<213> ORGANISM: Artificial Sequence
<220> FEATURE:
<223> OTHER INFORMATION: RNA aptamer

<400> SEQUENCE: 2
augcaguuug agaagucgcg cau                                23

<210> SEQ ID NO 3
<211> LENGTH: 23
<212> TYPE: DNA
<213> ORGANISM: Artificial Sequence
<220> FEATURE:
<223> OTHER INFORMATION: DNA aptamer

<400> SEQUENCE: 3
atgcagtttg agaagtcgcg cat                                23
```

LONG ACTING FORMULATION OF BIOPHARMACEUTICAL

CROSS REFERENCE TO RELATED APPLICATION

The present application is a continuation Application under 35 U.S.C. 120 of PCT/KR2007/005179, filed Oct. 22, 2007.

BACKGROUND OF THE INVENTION (a) Field of the Invention

The invention relates to a long-acting formulation of biopharmaceutical, more specifically an aptamer therapeutics. A branch-type PEG or a hyaluronic acid (HA) derivative of which degradation in vivo is regulated is linked by the bioconjugation with biopharmaceutical. The new formulation of aptamer therapeutics improves the function of aptamer therapeutics and patient compliance, thereby improving quality of medical service.

(b) Description of the Related Art

Aptamers are nucleotide molecules having specific binding affinity to molecules through interactions other than classic Watson-Crick base pairing.

Aptamers, like peptides generated by phage display or monoclonal antibodies ("mAbs"), are capable of specifically binding to selected targets and modulating the target's activity, e.g., through binding aptamers may block their target's ability to function. Created by an in vitro selection process, called as systemic evolution of ligands by exponential enrichment (SELEX), from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with subnanomolar affinity, and discriminates against closely related targets (e.g., aptamers will typically not bind to other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antibody-antigen complexes.

The first FDA-approved aptamer therapeutics of Macugen (pegaptanib) by Pfizer and Eyetech Co. in 2004 was a PEGylated vascular endothelial growth factor inhibitor for the treatment of age-related macular degeneration. It is reported that the risk of sightless person administered by Macugen® decreases to a half after the administration.

When the good aptamer therapeutics are administered parenterally in vivo, they are removed by the degradation with nuclease and by the rapid renal clearance in a few minutes. To overcome the short half-life, a chemical conjugation of the aptamer to poly-L-Lysine, polyamide, long chained alcohol, cholesterol and other steroids, phospholipid and peptide, etc. has been reported. In addition, PEG conjugation of the aptamer increases 10 times of half-life in vivo, and thus the aptamer can be used for therapeutically-active therapeutics. PEG includes a moiety of HO—(—$CH_2CH_2O$)n-H, and has been widely used for a long-acting formulation of biopharmaceutical.

It has been reported that an aptamer linked to two molecules of a 20 kDa PEG polymer in branch form has longer half-life than an aptamer linked by a 40 kDa PEG polymer, and thus has been used for most aptamer therapeutics (WO2006/029258).

PEGylation reagent where polyethylene glycol is linked to two amine residues of lysine via a peptide bond is commercially sold by Nektar. Urethane bond instead of the peptide bond in such product largely increases the stability of aptamer therapeutics (US 2003/0114647). Commercial PEGylated interferon of PEGASYS (trademark) produced by ROCHE is a PEGylated product with the branch-typed PEGlyation reagent sold by Nektar to largely increase bioavailability.

SUMMARY OF THE INVENTION

The present invention provides a new long-acting formulation of biopharmaceuticals such as aptamer specifically binding to a target molecule, protein and peptide.

An object of the present invention is to provide a PEGylation reagent for producing a branch-type PEGylated compounds by introducing bis-amine group to glycine or ethanolamine with cyanoethylation, and linking PEG to each amine group.

Therefore, the present invention relates a compound represented by chemical formula 1, and more preferable PEGylated aptamer conjugate, and a method therefore.

Chemical formula 1

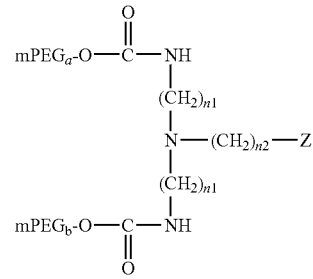

wherein, mPEGa and mPEGb are independently monomethoxy polyethylene glycol having molecular weight of 100 to 100,000 Da;

n1 is an integer of 1 to 10; n2 is an integer of 0 to 10; and Z is —OH, —COOH, —O—C(O)—O—Cl,

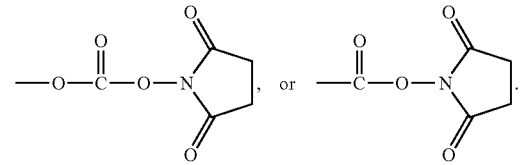

The polymer further contains protein, enzyme, nucleotide, lipid, liposome, solid surface, or particle including a functional group being capable of reacting with Z, and more preferably an oligonucleotide aptamer in length of 30 to 45 nucleotides.

Another object of the present invention is to provide a method of preparing a PEGylation reagent comprising the steps of: performing an amine group of glycine with cyanoethylation to produce two cyano moieties; reducing the cyano moieties to amine groups; forming urethane bond by reacting each amine group with monomethoxy polyethylene glycol (mPEG) succinimidyl carbonate; and obtaining PEGylation reagent by reacting with N-hydroxysuccinimide (NHS).

Further object of the present invention is to provide a method of preparing a PEGylation reagent comprising the steps of: performing an amine group of ethanolamine with cyanoethylation to produce two cyano moieties; reducing the cyano moieties to amine groups; forming urethane bond by reacting each amine group with monomethoxy polyethylene glycol (mPEG) succinimidyl carbonate; substituting terminal alcohol group with acid chloride group by reacting with triphosphazine; and obtaining the PEGylation reagent by reacting with N-hydroxysuccinimide (NHS).

Still further object of the present invention is to provide by introducing two or more functional groups to phosphoramidite compound, synthesizing oligonucleotide aptamer by using the same, and linking PEG to the terminus of the synthesized oligonucleotide to obtain long-acting formulation of aptamers.

The fourth object of the present invention is to provide a new long-acting formulation by using a hyaluronic acid (HA) derivative, of which degradation in vivo is suppressed or regulated, linked by the bioconjugation with biopharmaceutical aptamer. In specific embodiment, the present invention provides a hyaluronic acid-aptamer conjugate by linking an aptamer with HA derivative of which a terminal carboxyl group is reacted with adipic acid dihydrazide (ADH), tris(2-aminoethyl)amine (TREN), 2-aminoethyl methacrylate, or N-(3-Aminopropyl) methacrylamide hydrochloride (APMAm).

The fifth object of the present invention is to provide a long-acting formulation by using HA-ADH derivative which is prepared by reacting ADH to a carboxyl group of hyaluronic acid in a mixed solvent of water and an organic solvent. The degradation in vivo of HA-ADH is regulated or suppressed.

In the sixth object of the present invention, the hyaluronic acid is modified with 2-aminoethyl methacrylate (AEMA) or-(3-Aminopropyl) methacrylamide hydrochloride (APMAm) in an organic solvent to produce HA-AEMA or HA-APMAm. HA-AEMA or HA-APMAm is linked to an aptamer containing thiol group with Michael addition to obtain a long-acting aptamer therapeutic.

BRIEF DESCRIPTION OF THE DRAWINGS

For a more complete understanding of the present invention, and the advantages thereof, reference is now made to the following descriptions taken in conjunction with the accompanying drawings, in which:

FIG. 4A for anti-VEGF 2'-OMe-RNA aptamer, FIG. 4B for PEGylated anti-VEGF 2'-OMe-RNA aptamer, and FIG. 4C for anti-VEGF DNA aptamer.

DETAILED DESCRIPTION OF THE PREFERRED EMBODIMENTS

Figure 1:
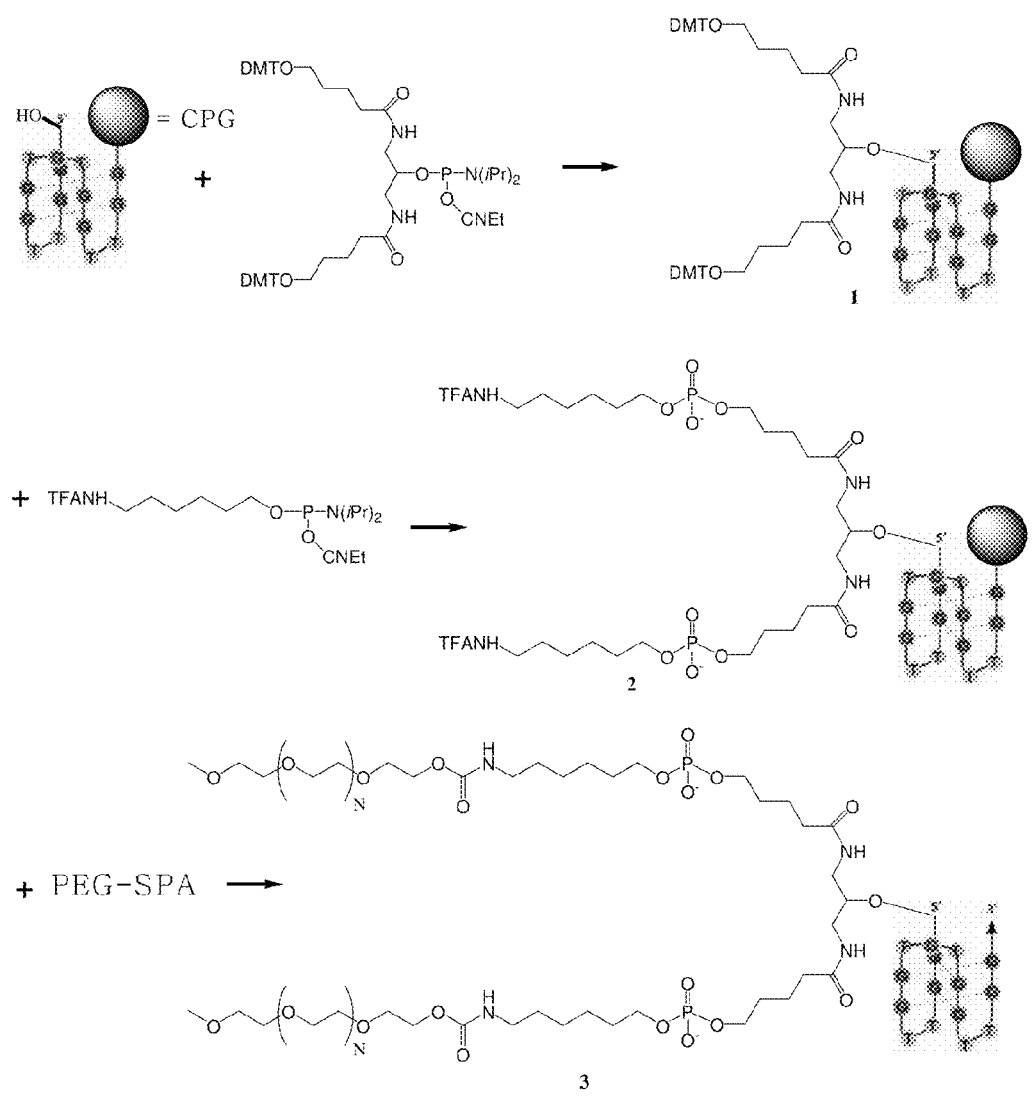
FIG. 1 is a schematic drawing showing synthesis of branched PEGylated aptamer using bis-amine modified oligonucleotide (CPG=Controlled Pore Glass).

These and other objects of the invention will be more fully understood from the following description of the invention, the referenced drawings attached hereto and the claims appended hereto.

To develop a new long-acting formulation of biopharmaceuticals such as aptamer specifically binding to a target molecule, protein and peptide, the present invention relates to a PEGylation reagent for aptamer, a method of preparing PEGylated aptamer using phosphoramidite derivatives, HA derivatives with regulated degradation in vivo such a HA-ADH, HA-TREN, HT-AEMA and HA-APMAm, a conjugate of biopharmaceutical and the HA derivatives.

The present invention will be described in detail

1. Development of Branch-Type PEGylation Reagent

Two cyano moieties are produced by performing cyanoethylation at a bis-amine group of ethanolamine or glycine, reduced into amine groups, and reacted with polyethylene glycol succinimidyl carbonate to produce strong urethane bond. The carboxyl group is activated with NHS, and conjugated with aptamer having amine group.

The present invention relates to a method of preparing a PEGylation reagent comprising the steps of: performing an amine group of ethanolamine with cyanoethylation to produce two cyano moieties; reducing the cyano moieties to amine groups; forming urethane bond by reacting each amine group with monomethoxy polyethylene glycol (mPEG) succinimidyl carbonate; substituting terminal alcohol group with acid chloride group by reacting with triphosphazine; and obtaining the PEGylation reagent by reacting with N-hydroxysuccinimide (NHS). The representative branch-type PEGylation reagent is a compound of chemical formula 1:

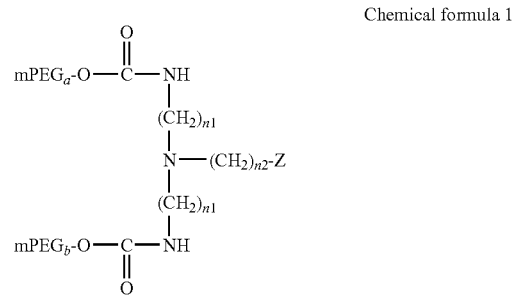

Chemical formula 1 wherein, mPEGa and mPEGb are independently monomethoxy polyethylene glycol having molecular weight of 100 to 100,000 Da;

n1 is an integer of 1 to 10; n2 is an integer of 0 to 10; and Z is —OH, —COOH, —O—C(O)—O—Cl, or

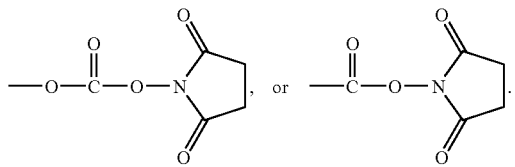

The preferred compound represented by chemical formula I is compounds of chemical formula 2a, chemical formula 2b, chemical formula 3a, chemical formula 3b, and chemical formula 3c.

As shown in reaction schemes 1 and 2, the branch-type PEGylation reagent is prepared by introducing bis-amine group to glycine or ethanolamine with cyanoethylation, and reacting with polyethylene glycol.

mPEGa and mPEGb is the same or different monomethoxy polyethylene glycol, and independently have a molecular weight of 100 to 100,000 Da, and more preferably 10,000 Da to 60,000 Da, for examples 10,000 Da, 20,000 Da, 40,000 Da, or 60,000 Da.

Chemical formula 2a

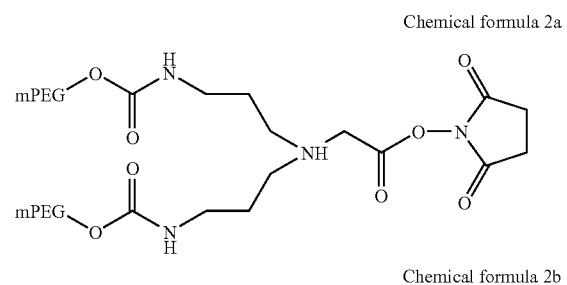

Chemical formula 2b

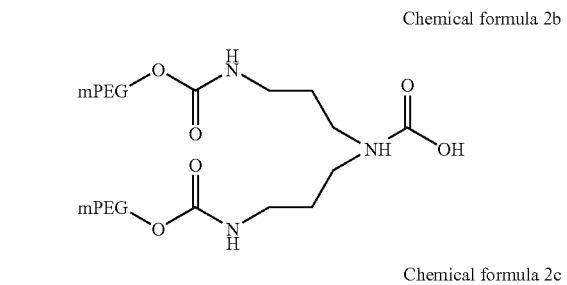

Chemical formula 2c

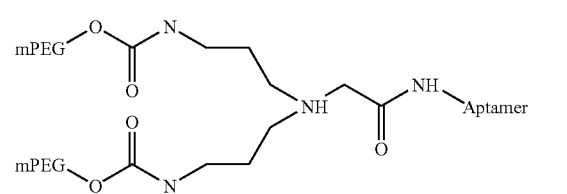

Reaction Scheme 1

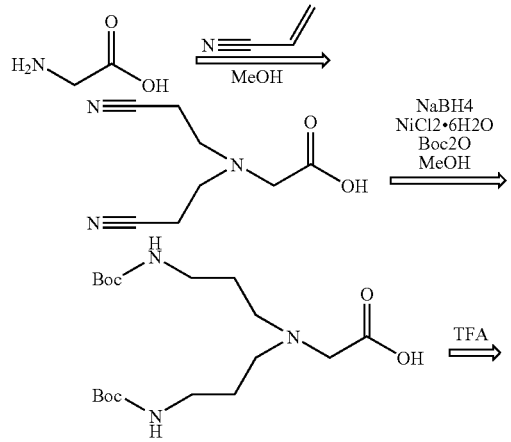

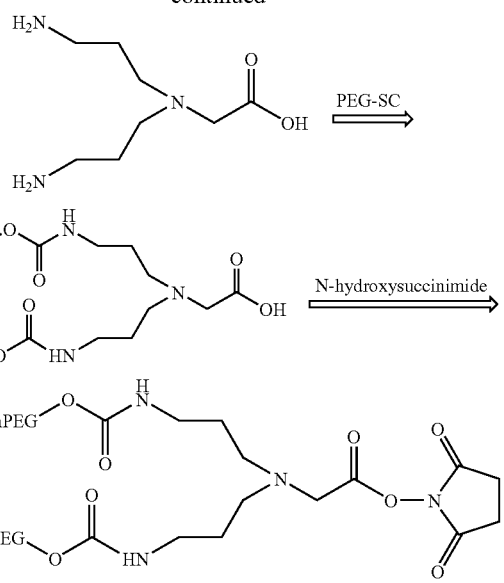

*PEG-SC: polyethyleneglycol succinimidyl carbonate

Chemical formula 3a

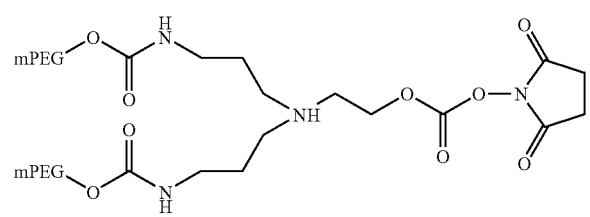

Chemical formula 3b

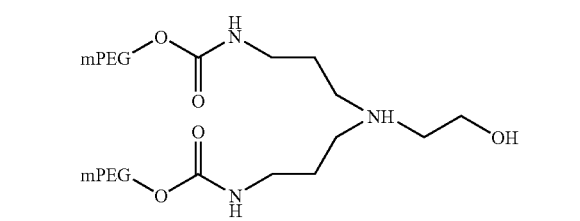

Chemical formula 3c

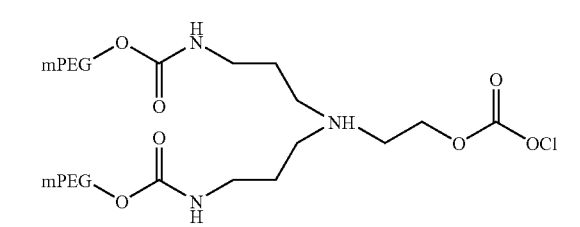

Chemical formula 3d

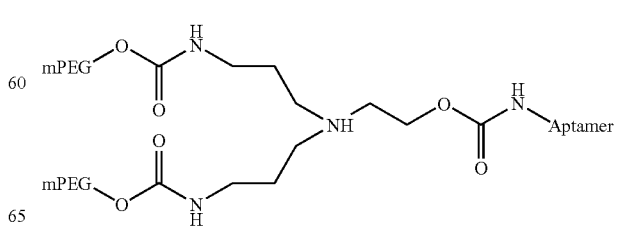

Reaction Scheme 2

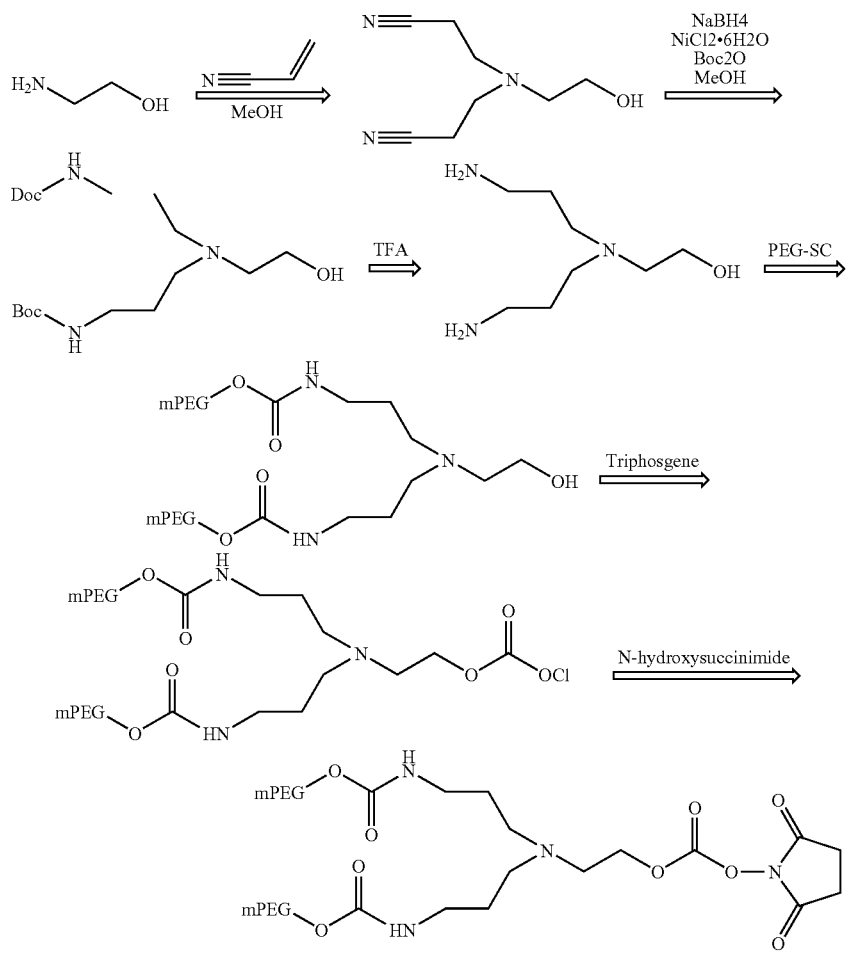

*PEG-SC: polyethyleneglycol succinimidyl carbonate

The polymer further comprises protein, enzyme, nucleotide, lipid, liposome, solid surface, or particle including a functional group being capable of reacting with Z, and more preferably aptamer.

The aptamer of the invention is any kind of aptamer but not limited to. Exemplary aptamer of oligonucleotide includes modified or non-modified DNA, RNA, or DNA/RNA hybrid, but not limited thereto. A biopharmaceuticals of the present invention, particularly aptamer contained in a therapeutic or pharmaceutical composition is referred to active or therapeutic material dissolved or dispersed in a pharmaceutically acceptable carrier or diluant in an effective amount. The carriers or diluents include any solvent, dispersing medium, coating, antibiotic agent, antifungal agent, isotonic agent, and absorption retarding agent, and the like. A supplemental active agent can be contained in the composition of the present invention.

The pharmaceutical composition can be prepared by a skilled person in this art in accordance with the general preparation method of pharmaceutical composition. In general, the composition can be formulated in forms of solution or suspension; injectable solution, solid formulation, or suspension; tablet, or solid formulation suitable for enteral administration; time release capsule; cream, lotion, salve, or inhalant.

The formulation can be administered in a pharmaceutically effective matter according to a general method. The formulation can be administered in various routes, for examples injection or capsule. The administration amount of active agent can be varied depending on the subject. The amount of active agent can be determined by a doctor.

2. Preparation of Branch-Type Aptamer with Two PEG Molecules

In one embodiment, by using phosphoramidite including two or more functional groups, the oligonucleotide aptamer is synthesized and linked with biopolymer such as PEG at terminal functional group to obtain a long-acting formulation of aptamer therapeutics.

Commercially-available branched phosphoramidite is dendrimeric phosphoramidite having terminal hydroxyl group provided by Glen research. The dendrimeric phosphoramidite is linked with PEGylation reagent to form ester bond which is easily degraded in vivo. In the present invention, two functional groups in three functional groups of core molecule are attached by PEG, and one functional group is combined with biopharmaceuticals such as aptamer, peptide, and protein to produce a long-acting formulation.

In one embodiment, branched oligonucleotide aptamer is synthesized by using two phosphoramidite derivatives. More specifically, aptamer conjugate linked with two PEG is prepared by coupling symmetric doubler phosphoramidite to 5'-terminus of an oligonucleotide aptamer synthesized using solid phase phosphoramidite chemistry, introducing a terminal amine group of the linked doubler phosphoramidite, and combining the PEG with the terminal amine group.

Chemical formula 4

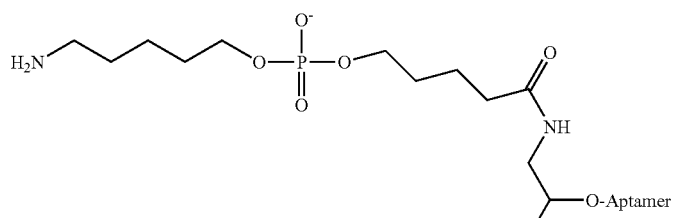

Chemical formula 5

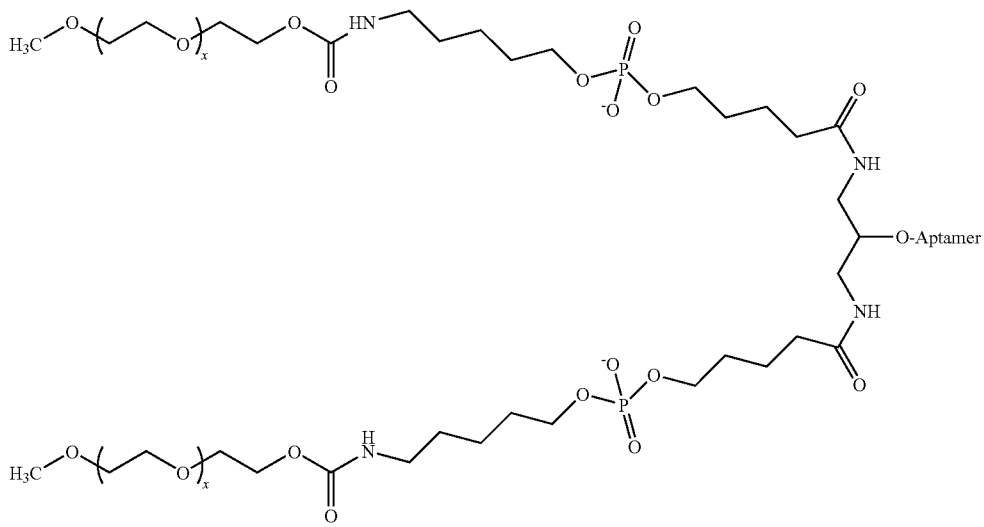

In reaction scheme 3, two functional groups are introduced to aptamer by using phosphoramidite having branch-type amine groups, and then two PEG molecules are reacted.

In one embodiment, the preparation method is performed by coupling symmetric doubler phosphoramidite to 5'-terminus of an oligonucleotide aptamer synthesized using solid phase, reacting with 5'-amino modifier-C6, and linking PEG to terminus of phosphoramidite to produce branched aptamer conjugate having two PEG molecules at its terminus.

Reaction Scheme 3

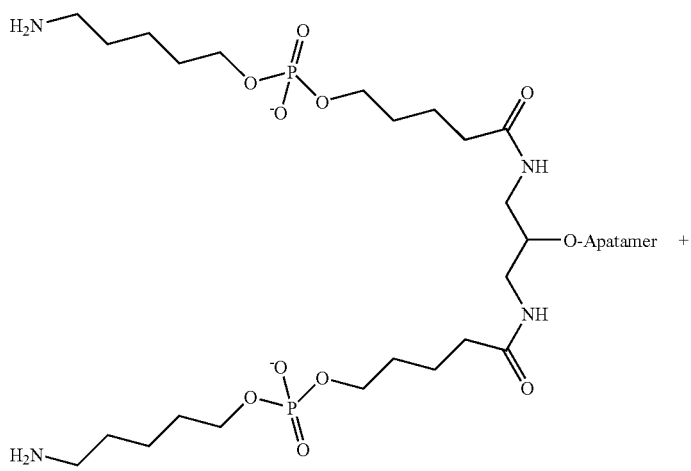

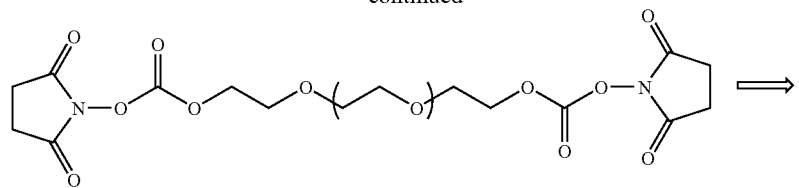

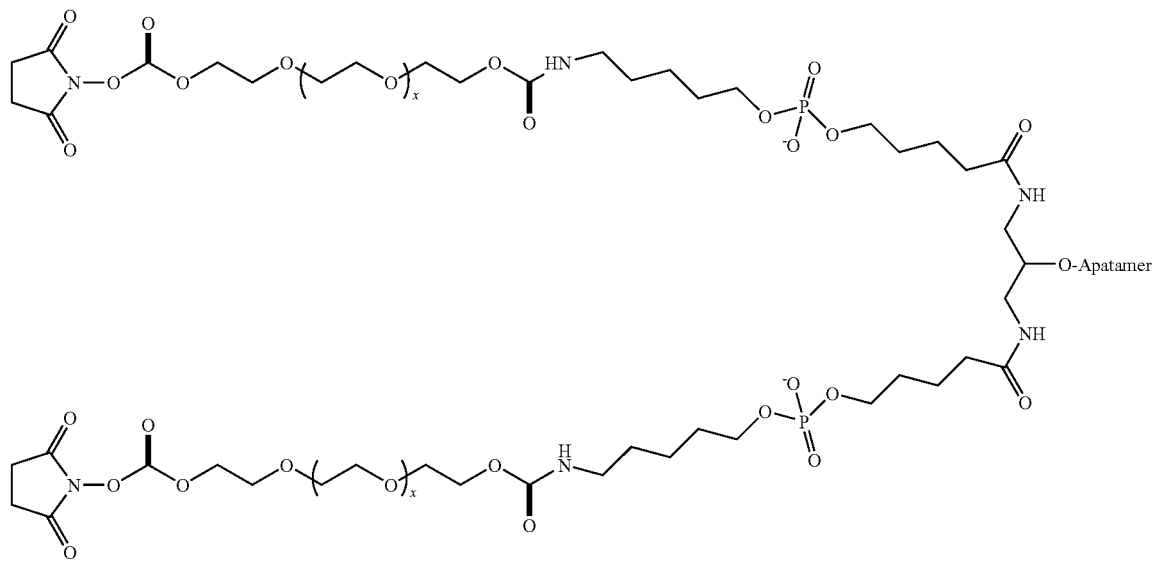

In chemical formula 5, x is an integer of 170 to 350.

In one embodiment, branched 40KD PEG is introduced to the oligonucleotide aptamer by reacting with two 20KD mPEG succinimidyl propinonate. For example, symmetric doubler phosphoramidite(10-1920-02) provided by Glen research is introduced to the oligonucleotide aptamer, and then, reacted with 5'-amine-modifier-C6-TFA(10-1016-02) to obtain the aptamer having two amine groups.

3. Bioconjugation of Hyaluronic Acid Derivative and Aptamer

In another embodiment, HA derivative is obtained by reacting carboxyl group of hyaluronic acid with adipic acid dihydrazide (ADH), tris(2-aminoethyl)amine (TREN), 2-aminoethyl methacrylate, or N-(3-Aminopropyl) methacrylamide hydrochloride (APMAm), and then conjugated with aptamer to produce a hyaluronic acid-aptamer conjugate.

Hyaluronic acid of the present invention is not particularly limited, for examples hyaluronic acid with molecular weight of 20,000 Da to 4,000,000 Da. In consideration of the molecular weight of hyaluronic acid, x+y is about 50 to 10,000 in following chemical formulae where x and y are integer of equal to or more than 1.

3-1. Preparation of Aptamer Conjugate with HA-Adipic Acid Dihydrazide (ADH)

Chemical formula 6a

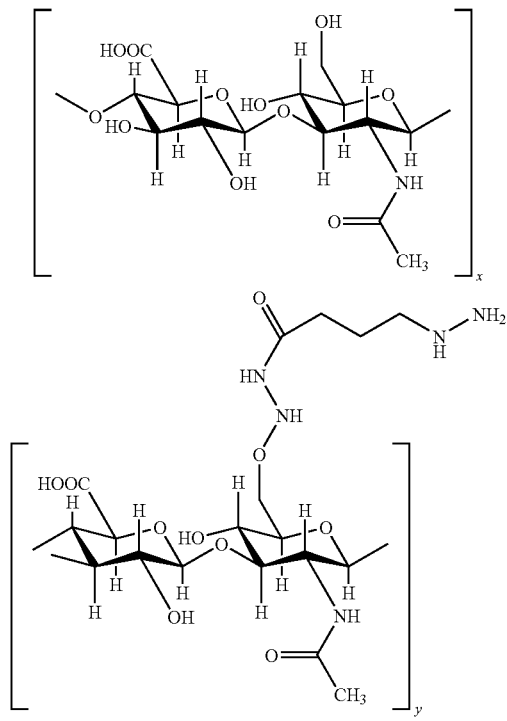

13
-continued
Chemical formula 6b
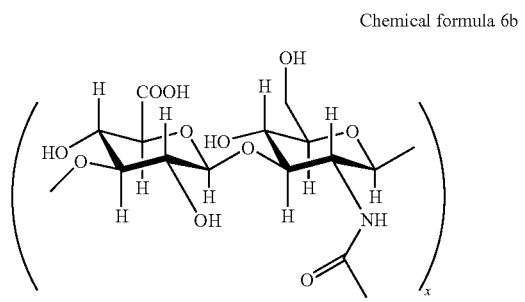
14
-continued
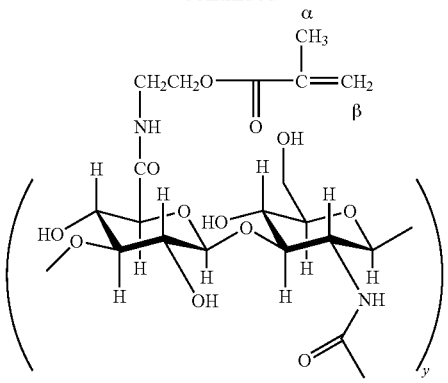
Reaction scheme 4 shows the conjugating reaction of HA-ADH and aptamer activated by N-hydroxysuccinimide (NHS) at its terminus.
Reaction Scheme 4
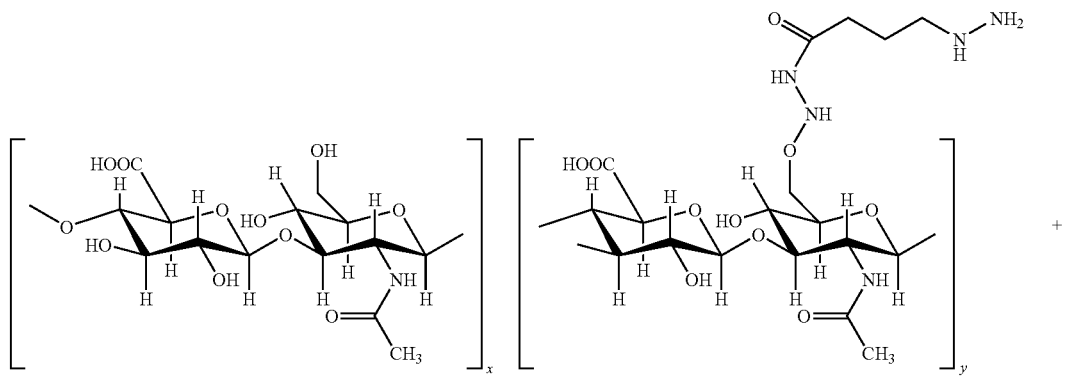
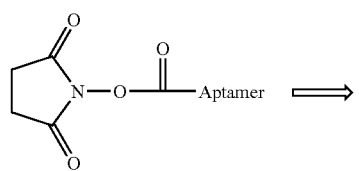
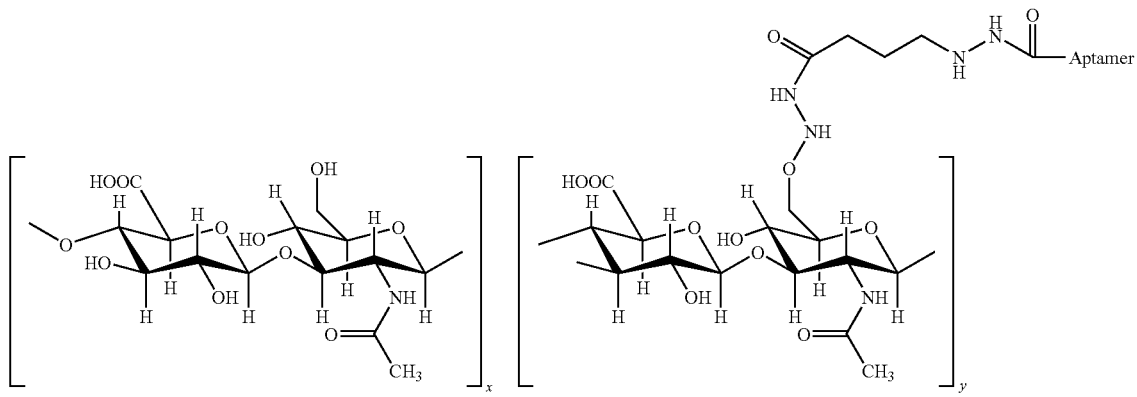

HA-ADH with regulated degradation in vivo is prepared by reacting ADH to a carboxyl group of hyaluronic acid in a mixed solvent of water and an organic solvent. In accordance with the preparation method as described above, HA-aptamer conjugate is prepared by using HA-ADH.

The organic solvent amount of mixed solvent is 1 to 90 mol %, and more preferably 25 mol % to 85 mol %. The exemplary organic solvent is ethanol.

3-2. Preparation of Aptamer Conjugate with HA-TREN

Reaction scheme 5 shows the conjugating reaction of HA-TREN and aptamer activated by N-hydroxysuccinimide (NHS) at its terminus.

Chemical formula 7

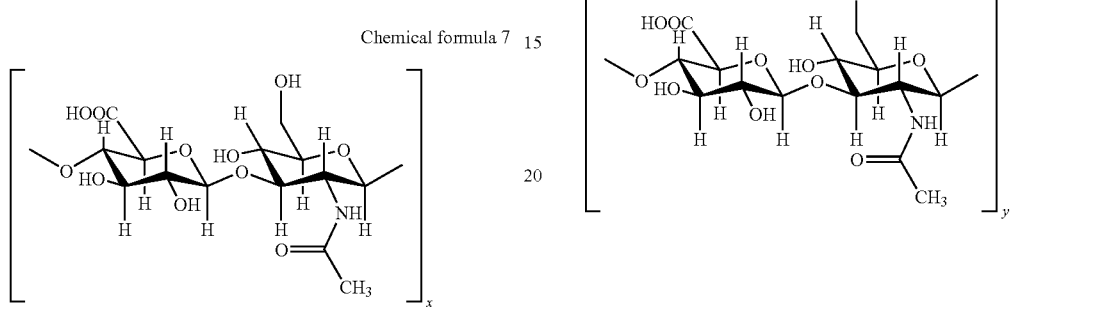

Reaction Scheme 5

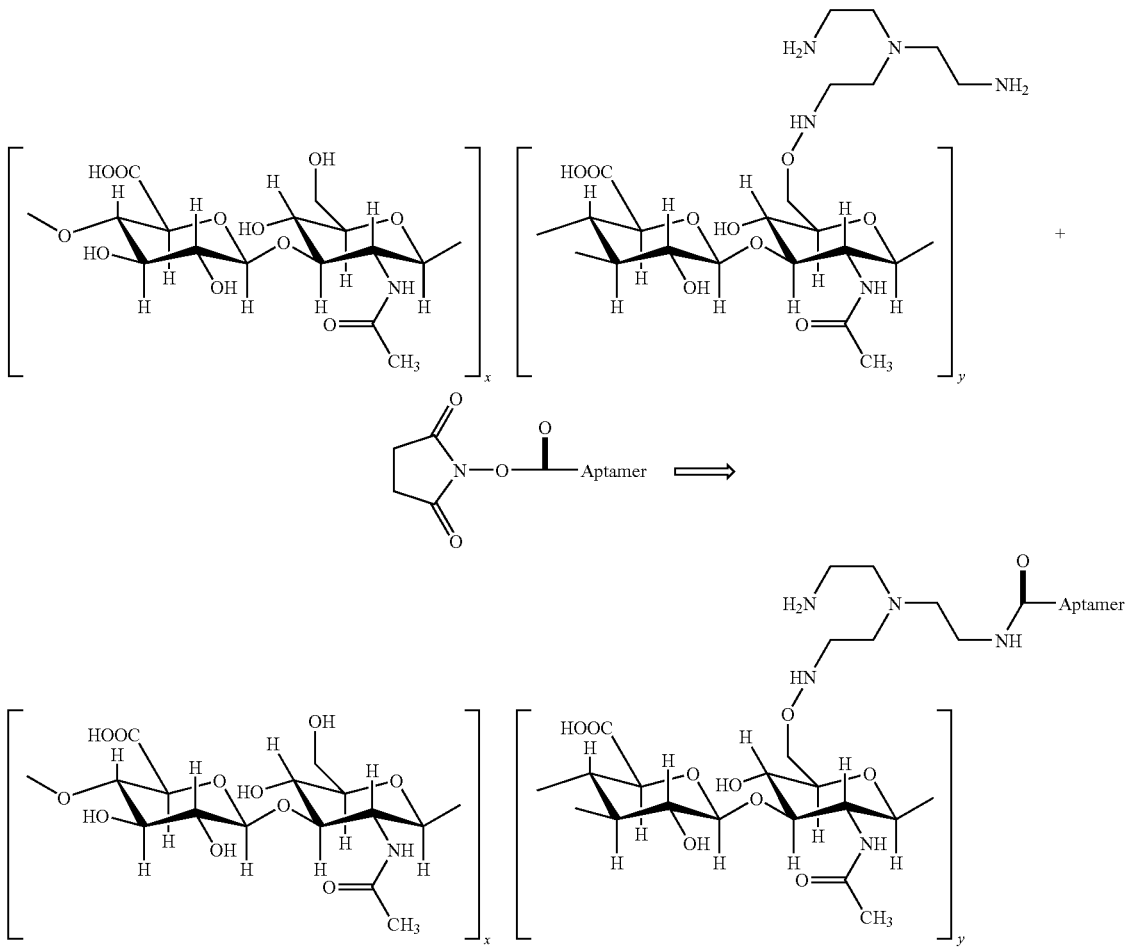

HA-TREN with regulated degradation in vivo is prepared by reacting TREN to a carboxyl group of hyaluronic acid in a mixed solvent of water and an organic solvent. In accordance with the preparation method as described above, HA-aptamer conjugate is prepared by using HA-TREN.

The organic solvent amount of mixed solvent is 1 to 90 mol %, and more preferably 25 mol % to 85 mol %. The exemplary organic solvent is ethanol.

3-3. Preparation of Aptamer Conjugate with HA-2-Aminoethyl Methacrylate (AEMA)

Synthesis of HA-AEMA is shown in Reaction Scheme 6a, and thiol group of aptamer is conjugated with Michael addition of HA-AEMA in Reaction Scheme 6b.

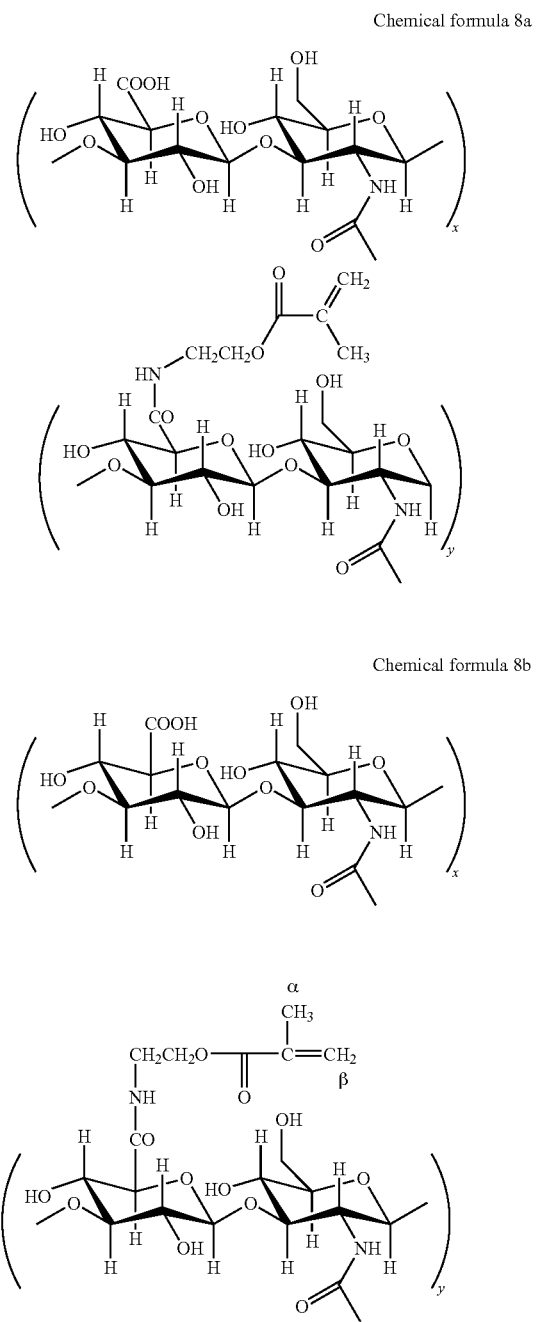

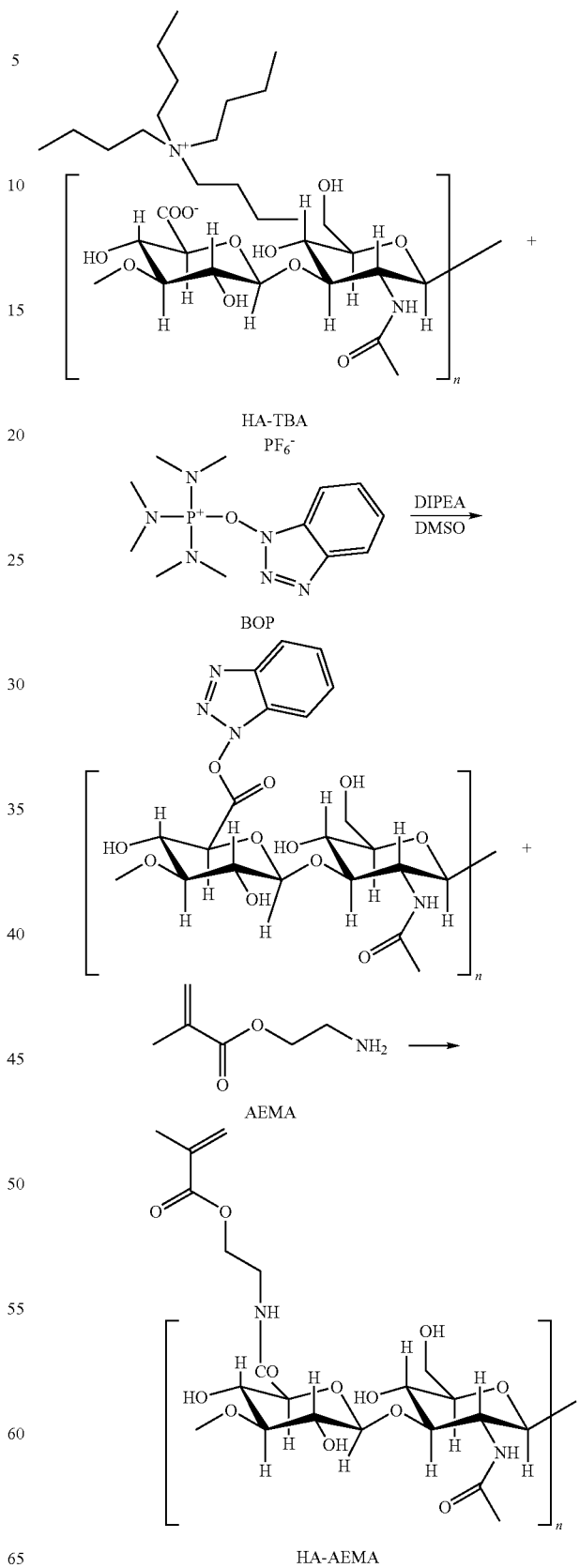

Reaction scheme 6b
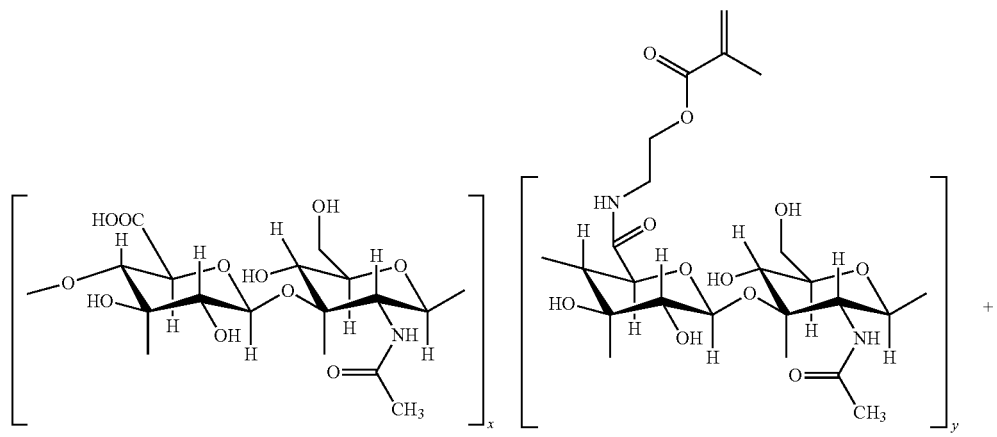
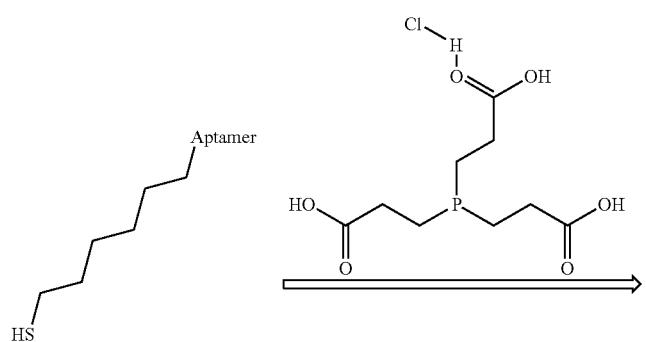
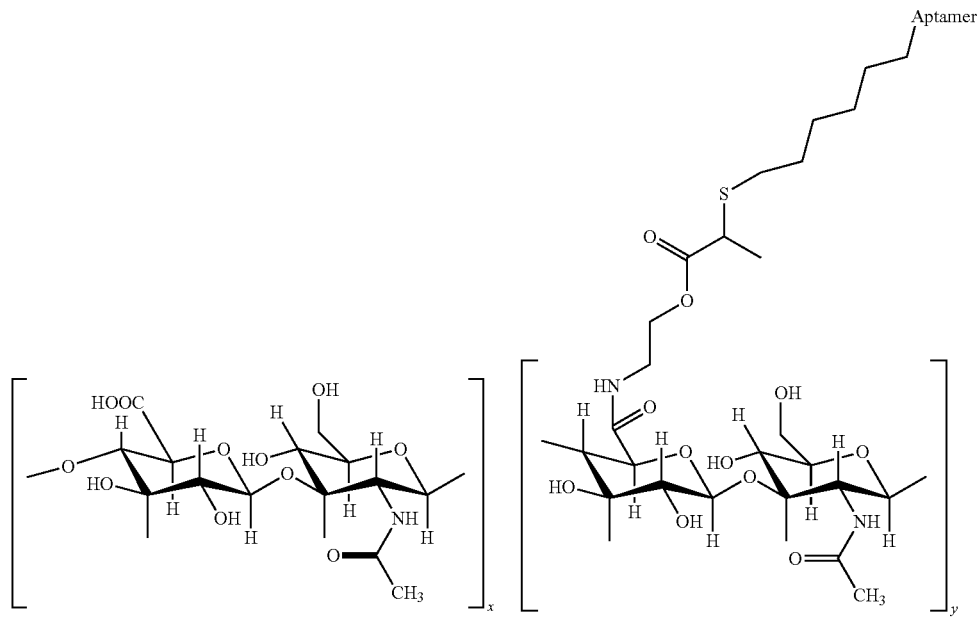

As illustrated in reaction scheme 6b, HA-AEMA is produced by chemically modifying hyaluronic acid with 2-aminoethyl methacrylate (AEMA), and is linked to an aptamer having thiol group at its terminus in the presence of Tri(2-carboxyethyl)phosphine hydrochloride (TCEP) to produce a long-acting formulation of aptamer therapeutics.

3-4. Preparation of Aptamer Conjugate with HA-(3-aminopropyl methacrylamide hydrochloride (APMAm)

Synthesis of HA-APMAm is shown in Reaction Scheme 7a, and thiol group of aptamer is conjugated with Michael addition of HA-APMAm in Reaction Scheme 7b.

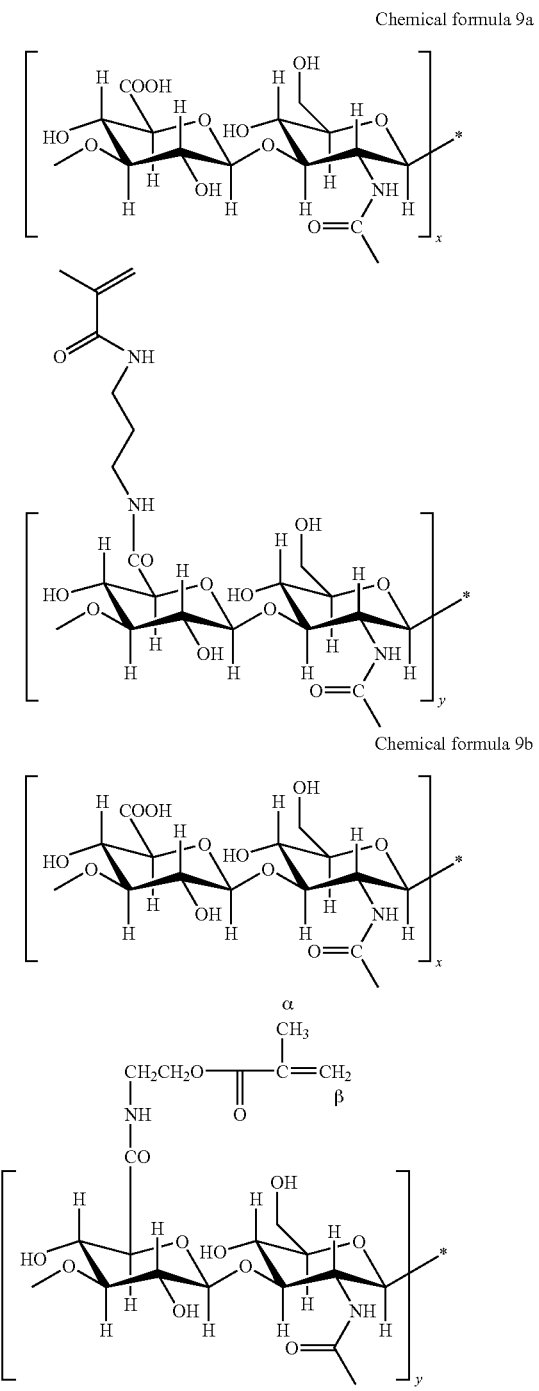

Chemical formula 9a

Chemical formula 9b

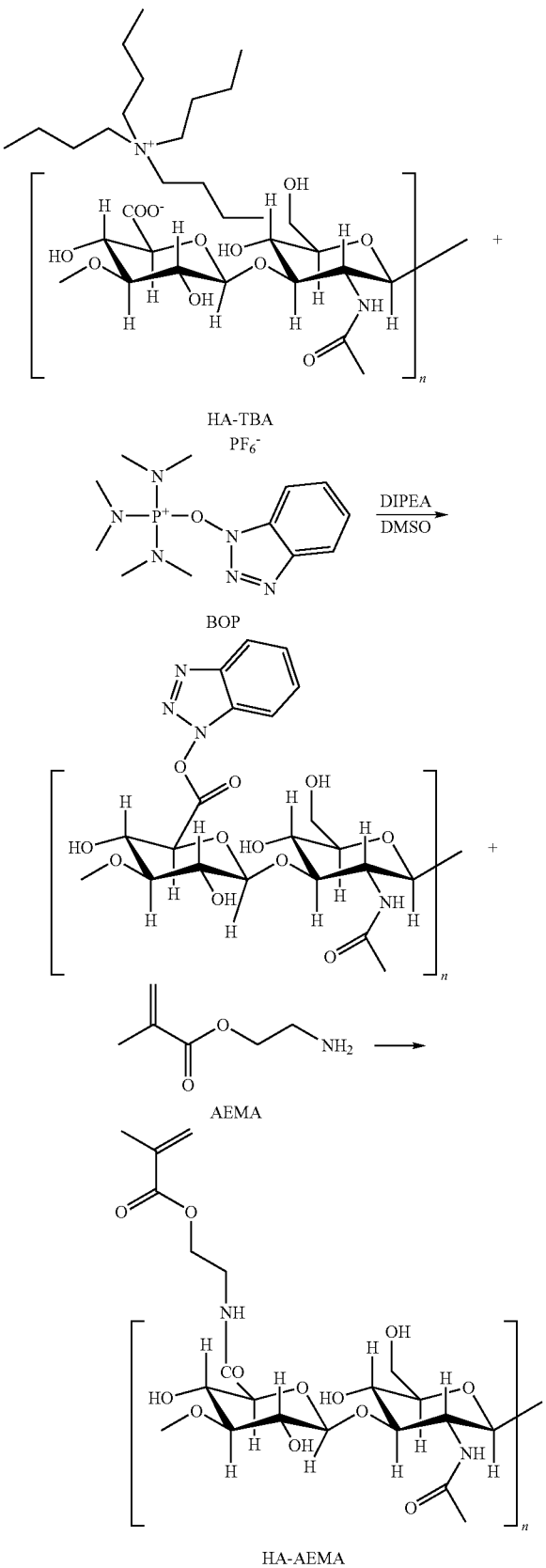

Reaction scheme 7a

Reaction scheme 7b
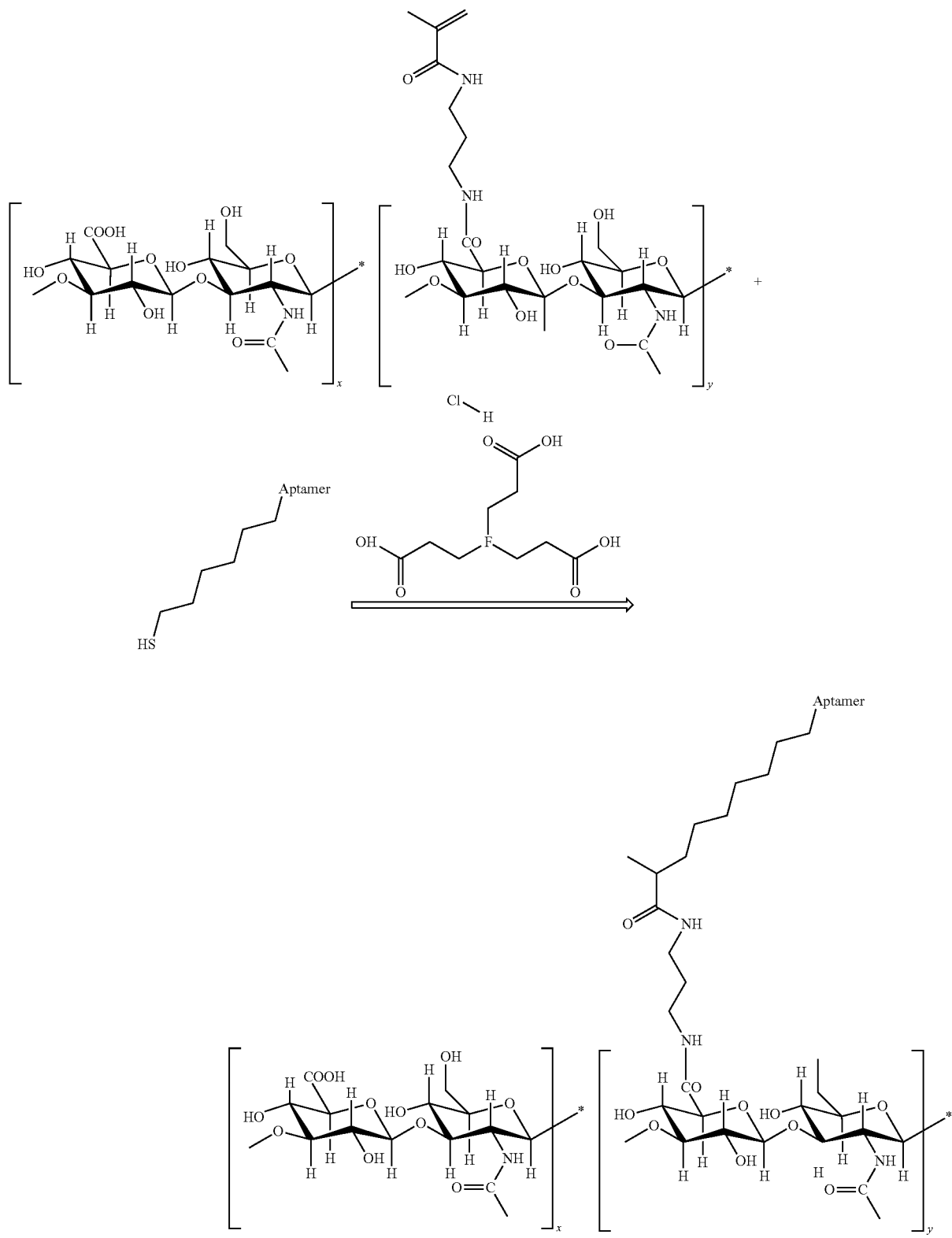
As illustrated in reaction scheme 7b, HA-APMAm is produced by chemically modifying hyaluronic acid with APMAm, and is linked to an aptamer having thiol group at its terminus in the presence of Tri(2-carboxyethyl)phosphine hydrochloride (TCEP) to produce a long-acting formulation of aptamer therapeutics.

4. Conjugation of PEGylated aptamer and HA-ADH
Aptamer having a PEG at a terminus or two PEG at two terminus is conjugated with HA-ADH in the following reaction scheme.
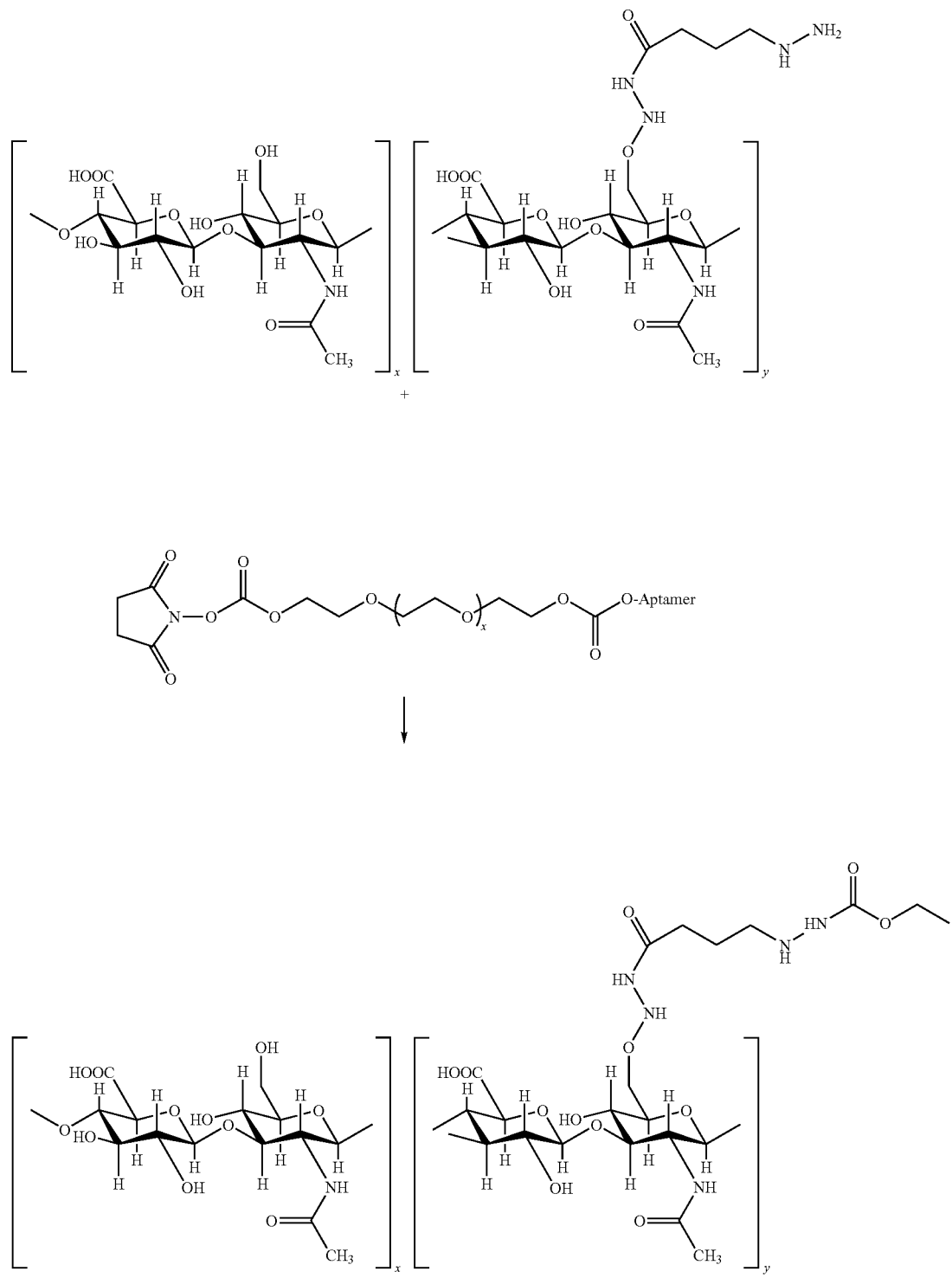
Reaction scheme 8

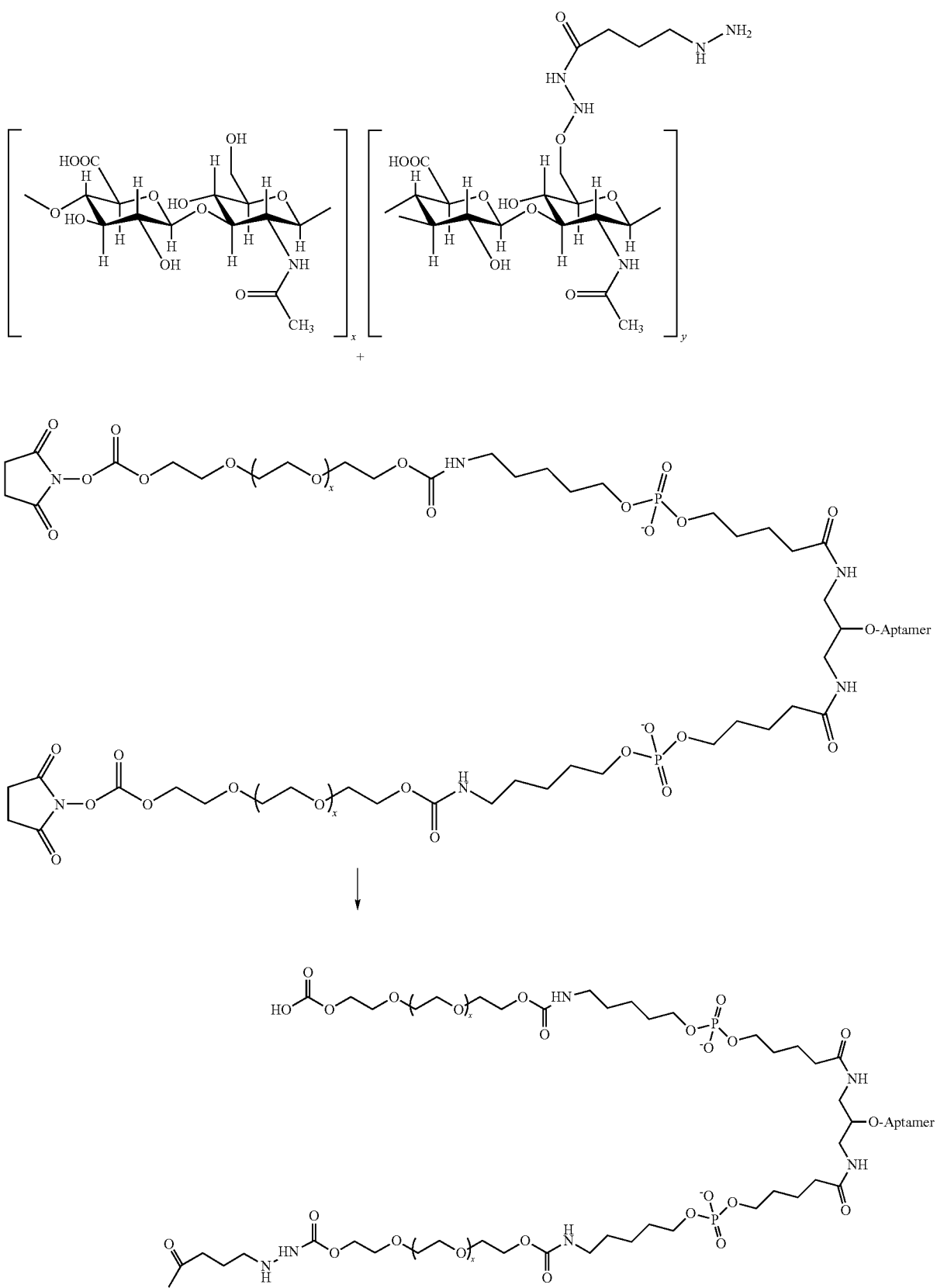

-continued

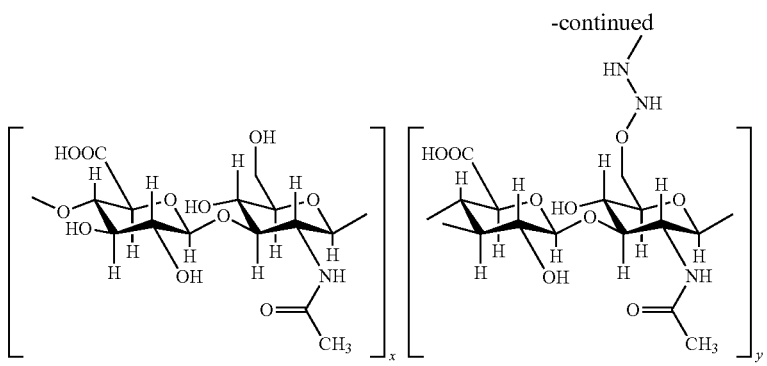

PEGylated aptamer or hyaluronic acid derivative-aptamer conjugate is filled into HA hydrogel or PLGA microsphere to produce slow-released formulation, thereby largely extending a half-life of aptamer. HA derivatives with regulated degradation in vivo can be developed as a delivery system of biopharmaceuticals such as aptamer and protein.

The present invention is further explained in more detail with reference to the following examples. These examples, however, should not be interpreted as limiting the scope of the present invention in any manner.

EXAMPLE 1

Preparation of PEGylation Reagent and PEGylated Aptamer Using the Reagent 1.1. PEGylation Reagent for a Compound of Chemical Formula 2a Chemical formula 2a

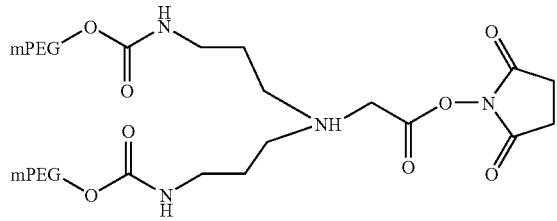

An aqueous solution of NaOH (2N, 50 mmol) was added to a suspension of lysine (50 mmol) in water (250 mL) and acrylonitrile (99 mL, 150 mmol) was added. The reactant was stirred 18 hours at 80 degree. The mixture carefully neutralized with an aqueous solution of HCl. The excess of acrylonitrile was removed with reduced pressure. The mixture was extracted with ether, and the organic extracts were washed with brine, then dried over $MgSO_4$, and concentrated to give dinitrile (34 mmol) as a fairly pure oil. To a dinitrile solution of 34 mmol in methanol 100 ml was added $NiCl_2.6H_2O$ (34 mmol) and di-tertbutyl dicarbonate (80 mmol). The resulting solution was stirred at room temperature and was added $NaBH_4$ (210 mmol) by portion. After stirring at room temperature for 12 hours, the suspension was filtered off by filter paper. The solution was evaporated in vacuo, and the residue was added ethyl acetate 300 ml. The solution was washed with water, 5% sodium dicarbonate solution and brine. The organic phase was dried over $MgSO_4$. The solution was filtered and purified by silica gel column chromatography using ethyl acetate:hexane (1:1) and gave (25 mmol) as a white solid.

Total yield: 50%;

1H $^1$H NMR (200 MHz, [D6]DMSO): δ=6.74 (t, 2H, NH), 3.30 (t, 1H, $CHCH_2CH$), 2.91 (td, 4H, $CH_2NH$), 2.56 (t, 4H, NCH2), 1.52 (m, 4H, NCH2CH2), 1.42 (m, 2H, $CHCH_2CH$), 1.37 (s, 18H, $C(CH_3)_3$)

The Boc group was then cleaved by dissolving the product in 2 mL of TFA for 1 h at room temperature. TFA was removed under vacuum. Two mg of the linker was then reacted with 170 mg of mPEG-succinimidyl carbonate (mw=20K) in 3 mL of DMF. Acylation was complete after overnight stirring at room temperature. The solution was then diluted with 5 volumes of water, extensively dialyzed against distilled water, and lyophilized. The reactant 120 mg was dissolved in pyrimidine 10 ml and followed by the addition N-hydroxysuccinimide (3 mmol) and DCC (3 mmol). The resulting mixture was stirred for 2 hours at 45° C., and then at room temperature for 24 hours. The mixture was filtered through celite, and the solvent was removed in vacuo. The residue was recrystallized form 2-propanol to obtain compound of chemical formula 2a.

1.2. PEGylation Reagent for a Compound of Chemical Formula 3a

Chemical formula 3a

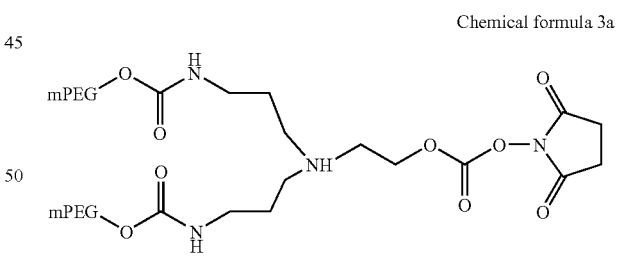

To a solution of ethanolamine (20 mmol) in methanol 30 ml was added acrylonitrile (30 mmol). The resulting solution was stirred at 70° C. for 3 hours, and the solvent was removed in vacuo. The residue was used without further purification. To a solution of dinitrile (30 mmol) in methanol 100 ml was added $NiCl_2.6H_2O$ (30 mmol) and di-tertbutyl dicarbonate (80 mmol). The resulting solution was stirred at room temperature and was added $NaBH_4$ (180 mmol) by portion. After stirring at room temperature for 12 hours, the suspension was filtered off by filter paper. The solution was evaporated in vacuo, and the residue was added ethyl acetate 500 ml. The solution was washed with water, 5% sodium dicarbonate solution and brine. The organic phase was dried over $MgSO_4$.

The solution was filtered and purified by silica gel column chromatography using Dichloromethane:MeOH (10:1) and gave (12 mmol) a yellow oil.

Total yield is 60%;

1H $^1$H NMR (200 MHz, D2O): δ=6.74 (t, 2H, NH), 3.30 (t, 1H, CHCH$_2$CH), 2.91 (td, 4H, CH$_2$NH), 2.56 (t, 4H, NCH2), 1.75 (m, 4H, NCH2CH2), 1.52 (m, 4H, NCH2CH2), 1.42 (m, 2H, CHCH$_2$CH), 1.37 (s, 18H, C(CH$_3$)$_3$)

Boc protected intermediate (16 mmol) was dissolved in dichloromethane 40 ml and added trifluoroacetic acid 20 ml. The resulting solution was stirred at room temperature for 3 hours. The solution was evaporated in vacuo, and coevaporated with ethanol. Two mg of the linker was then reacted with 170 mg of mPEG-succinimidyl carbonate (mw=20K) in 3 mL of DMF. Acylation was complete after overnight stirring at room temperature. The solution was then diluted with 5 volumes of water, extensively dialyzed against distilled water, and finally lyophilized (120 mg). Branched PEGylated alcohol 120 mg was dissolved in DMF 5 ml reacted with triphosgene (5 mmol) and N-hydroxysuccinimide (3 mmol) at 50 degree for 3 hours The residue was re-crystallized form 2-propanol to obtain compound of chemical formula 3a.

1.3. PEGylation of Aptamer

PEGylation reagents obtained from Examples 1.1 and 1.2 were used for performing PEGylation of the compounds of chemical formula 2a and chemical formula 3a.

Anti-thrombin DNA aptamers were synthesized using solid phase phosphoramidite chemistry with an automated oligonucleotide synthesizer. The aptamer sequence was 5'-d(GGTTGGTGTGGTTGG)-3' (SEQ ID NO:1).

5'-amino modifier-C6 was diluted as 0.1M solution in acetonitrile for terminal modification. The oligonucleotide was deprotected with ammonium hydroxide/methylamine (1:1) at room temperature for 12 hours and purified by ion exchange HPLC. Aptamer was dissolved to 2 mM in 100 mM sodium carbonate buffer, pH 8.5, and was reacted for 1 hour with a 2.5 molar excess of compound 1-1 (MW 40 kDa) in equal volumes of acetonitrile. The resulting products were then purified by reverse phase HPLC on Vydac C18 columns with acetonitrile, 50 mM TEAA as an eluant.

Same aptamer was dissolved to 2 mM in 100 mM sodium carbonate buffer, pH 8.5, and was reacted for 1 hour with a 2.5 molar excess of compound 1-2 (MW 40 kDa) in equal volumes of acetonitrile. The resulting products were then purified by reverse phase HPLC on Vydac C18 columns with acetonitrile, 50 mM TEAA as an eluant.

EXAMPLE 2

PEGylation of Anti-Thrombin Aptamer with Bis-Amine Terminal Groups

FIG. 1 is a schematic drawing showing synthesis of branched PEGylated aptamer using bis-amine modified oligonucleotide (CPG=Controlled Pore Glass).

2.1. Materials

DNA and modified phosphoramidite were purchased from Glenresearch, and mPEG-SPA was purchased from NOF Co., (Tokyo, Japan). The polymers were dried under vacuum prior to use. Organic synthesis reagents and solvents were purchased from Aldrich chemical Co. (Milwaukee, Wis.) and used without further purification.

2.2. Synthesis of Anti-Thrombin Aptamer with Bis-Amine Terminal Group

Anti-thrombin DNA aptamers were synthesized using solid phase phosphoramidite chemistry with an automated oligonucleotide synthesizer. The aptamer sequence was 5'-d(GGTTGGTGTGGTTGG)-3' (SEQ ID NO:1). The symmetric doubler phosphoramidite (Glenresearch. Cat. No. 10-1920) at a concentration of 0.1 M in acetonitrile was coupled to the terminal aptamer sequence.

The coupling time was about 15 minute for the doubler phosphoramidite addition. Then, 5'-amino modifier-C6 (Glenresearch. Cat. No. 10-1916) at a concentration of 0.2 M in acetonitrile was coupled to the terminal sequence (compound 2). The oligonucleotide was deprotected with ammonium hydroxide at room temperature for 12 hours and purified by ion exchange—high performance liquid chromatography (HPLC).

2.3. PEGylation of Anti-Thrombin Aptamer with Bis-Amine Terminal Groups

The modified DNA aptamer was dissolved at a concentration of 2 mM in sodium carbonate buffer (100 mM, pH 8.5) and was reacted for an hour with 5 molar excess of mPEG-SPA (MW 20 kDa) in equal volumes of acetonitrile (FIG. 1). The resulting product (compound 3) was purified by reverse phase HPLC with Vydac C18 column. Acetonitrile containing 50 mM TEAA was used as an eluant.

2.4. Branch-Type PEGylation of Anti-Thrombin DNA Aptamer

Figure 2:
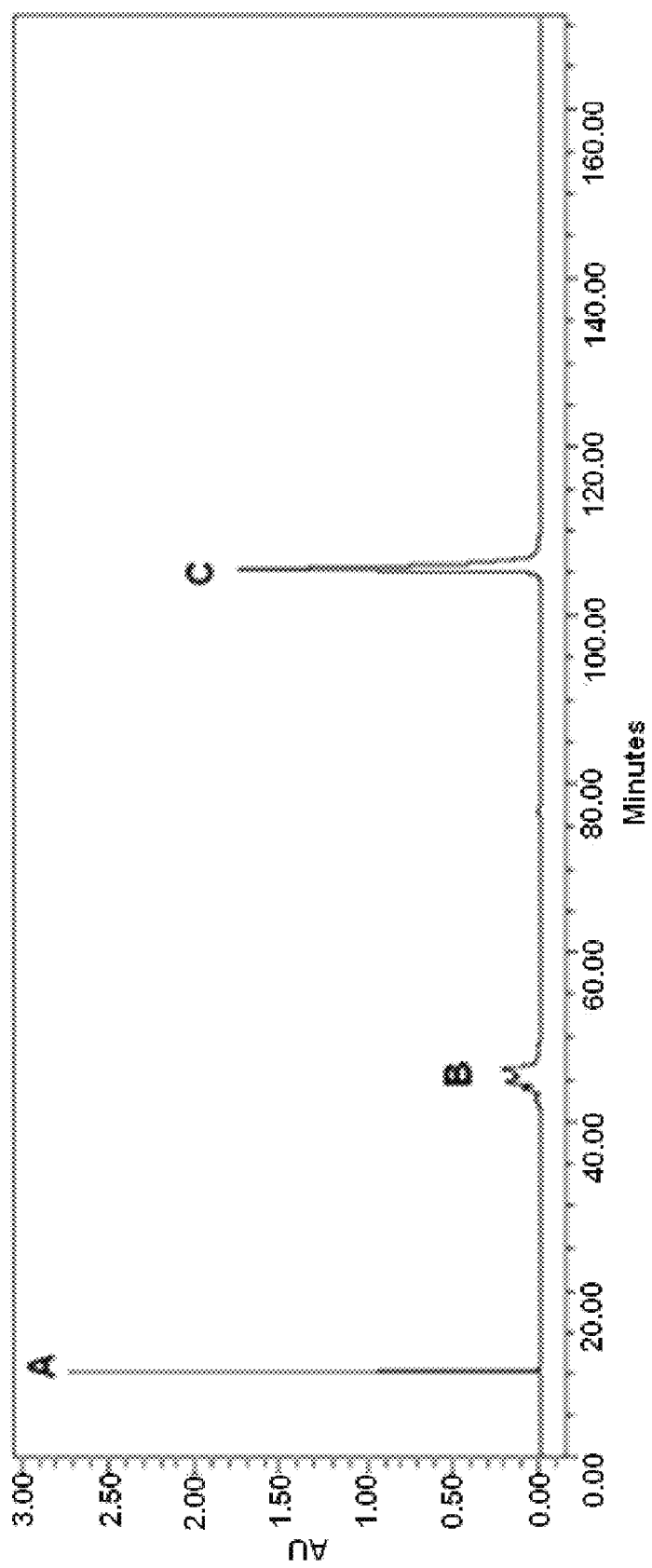
FIG. 2 is RP-HPLC result of PEGylation reagent (A), unreacted aptamer (B), and aptamer PEGylated with phosphoramidite derivative represented by chemical formula 5 in accordance with Example 2.

Anti-thrombin DNA Aptamer was used as a model for various aptamer therapeutics. A branch-type phosphoramidite and the following amine modified phosphoramidite synthon were successfully introduced to the final sequence of anti-thrombin aptamer. Then, the conventional linear PEGylation reagents were conjugated to the terminal amine group of oligonucleotide resulting in the branch-type PEGylated anti-thrombin DNA aptamer. The product was thought to be comparable to that by using the branch-type PEGylation reagent of NEKTAR Therapeutics. FIG. 2 shows the RP-HPLC of reaction products in an hour. FIG. 2 shows the RP-HPLC of reaction products in an hour. The unreacted PEG (peak A), anti-thrombin aptamer (peak B), and the PEGylated anti-thrombin aptamer (peak C) could be clearly separated on the RP-HPLC chromatogram. The final product of PEGylated anti-thrombin DNA aptamer could be obtained by the fractionation method.

EXAMPLE 3

Figure 3:
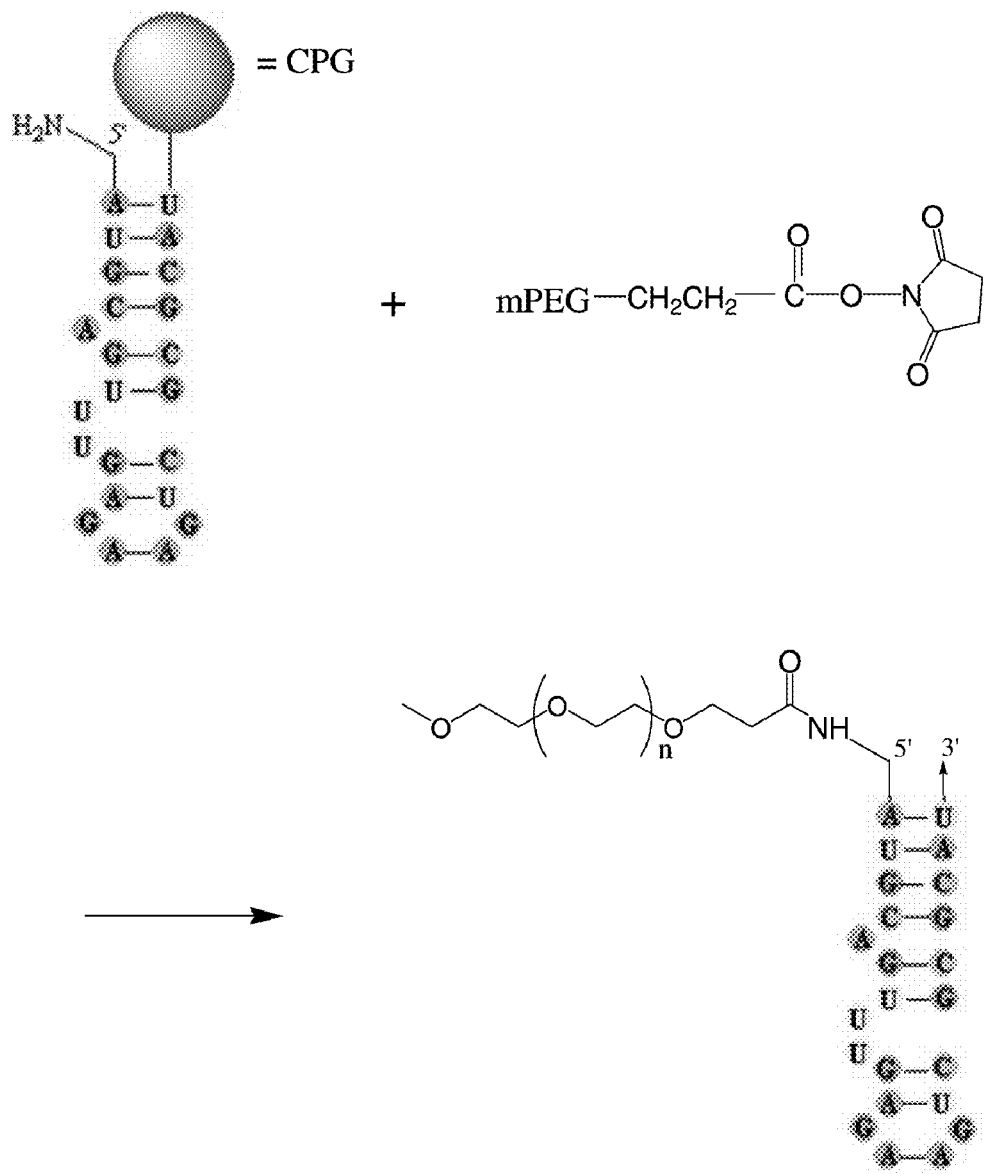
FIG. 3 is a schematic drawing showing synthesis of PEGylated anti-VEGF 2'-OMe-RNA aptamer (CPG=Controlled Pore Glass) in accordance with Example 3.

Change in Binding Affinity of PEGylation 3.1. Surface Plasmon Resonance (SPR) of Anti-VEGF Aptamer Samples to VEGF Coated on the BIAcore Chip Anti-VEGF 2'-OMe-RNA aptamer was synthesized using a solid phase phosphoramidite chemistry with an automated oligonucleotide synthesizer. The sequence of the aptamer was 5'-AmUmGmCmAmGmUmUmUmGmAmG-mAmAmGmUmCmGmCmGmCmAmU-3' (SEQ ID NO: 2). As a reference, DNA aptamer was also synthesized with the same sequence. (5'-AmTmGmCmAmGmTmTmTmG-mAmAmGmTmCmGmCmGmCmAmT-3') (SEQ ID NO:3). For a PEGylation, the anti-VEGF 2'-OMe-RNA aptamer with a 5' terminal amine group was dissolved at a concentration of 2 mM in sodium carbonate buffer (100 mM, pH 8.5) and reacted for an hour with 5 molar excess of methoxy-polyethylene glycol succinimidyl propionic acid (mPEG-SPA, MW 20 kDa) in equal volume of acetonitrile. The PEGylation was successfully carried out by the formation of the amide bond between the succinimidyl group of mPEG-SPA and the terminal amine group of anti-VEGF 2'-OMe-RNA aptamer (FIG. 3). FIG. 3 is SPR result showing a binding force of anti-VEGF aptamer to VEGF coated on BIAcore chip.

The biological activity of PEGylated anti-VEGF 2'-OMe-RNA aptamer was assessed by the measurement of binding affinity using surface plasmon resonance (SPR) analysis. SPR has been widely used for the detection of bio-affinity adsorption between the biomolecules such as DNA, RNA, and protein. The 20K PEGylated anti-VEGF 2'-OMe-RNA aptamer, purified by RP-HPLC fractionation method, was dissolved in phosphate buffered saline (PBS, pH=7.4) at a concentration of 500 nM. SPR analysis was performed using a BIAcore 2000 instrument. A series of diluted solutions of anti-VEGF 2'-OMe-RNA aptamer, PEGylated anti-VEGF 2'-OMe-RNA aptamer, and anti-VEGF DNA aptamer were passed over the immobilized VEGF on the chip. The adsorption of aptamers onto the VEGF resulted in the formation of aptamer-VEGF complex, which was detected by SPR before each injection, the surface of the chip was regenerated with 0.03% sodium dodecyl sulfate (SDS) and 50 mm sodium hydroxide (NaOH) containing 0.5 m sodium chloride (NaCl).

Figure 4A:
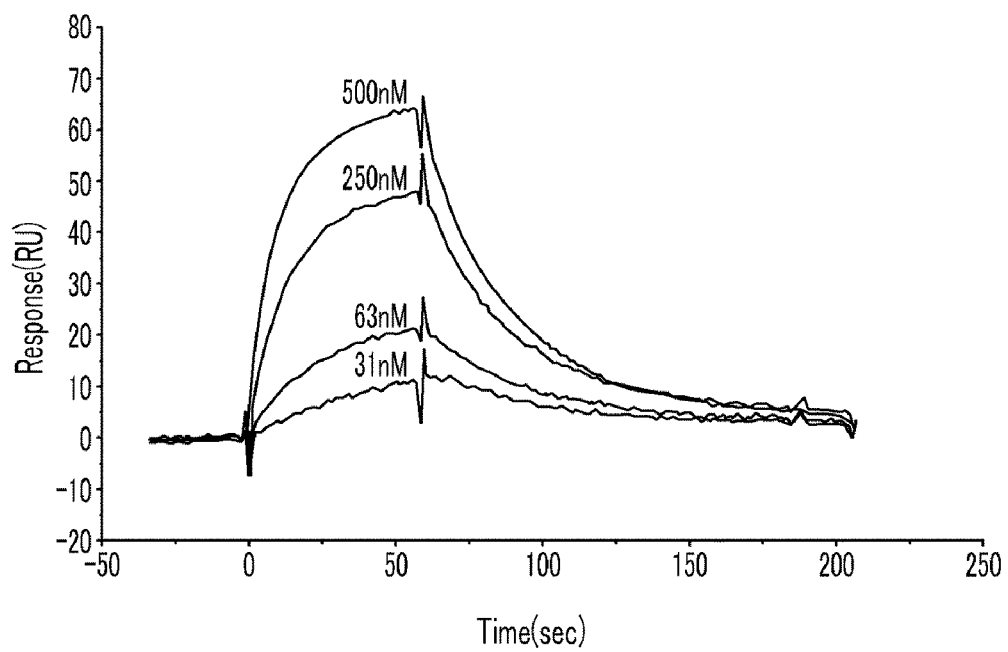
FIGS. 4A to 4C are SPR result showing a binding force of anti-VEGF aptamer to VEGF coated on BIAcore chip.
Figure 4B:
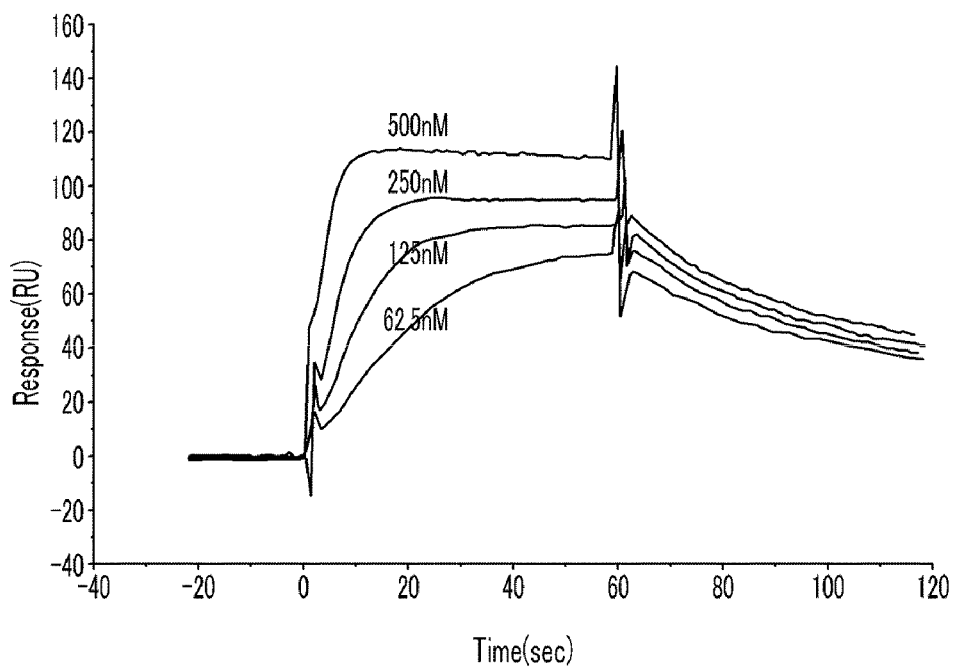
Figure 4C:
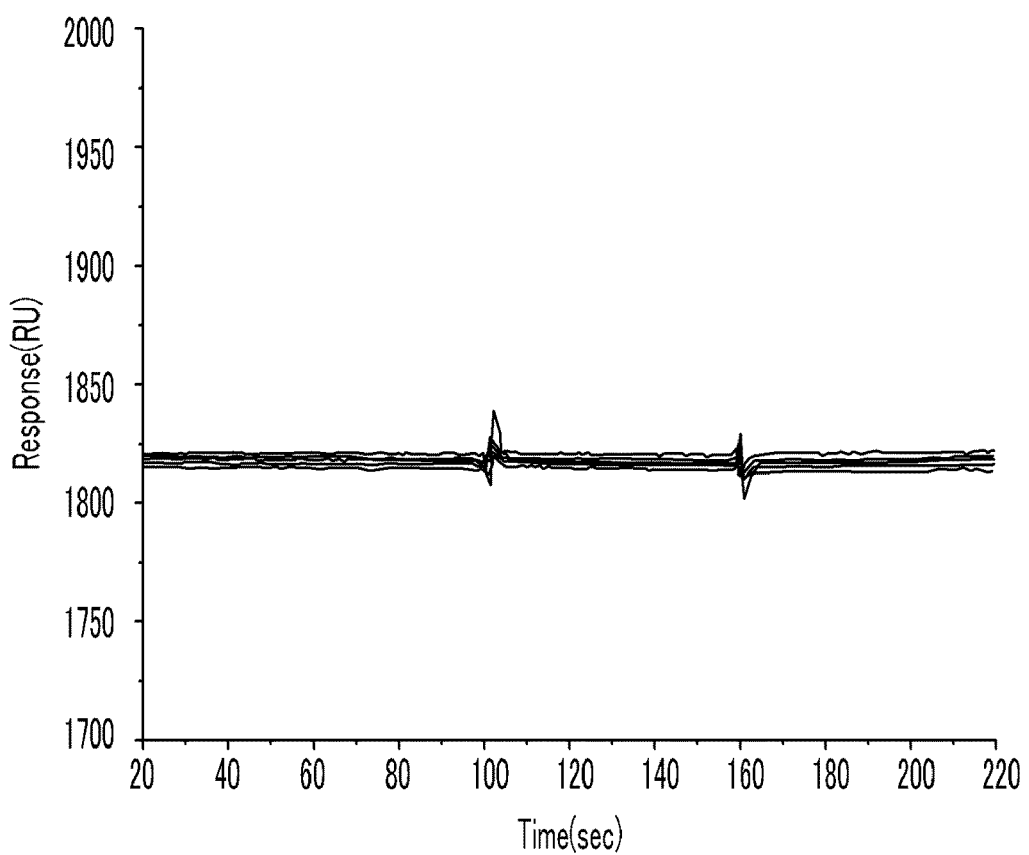

FIGS. 4a to 4c show the binding affinity of anti-VEGF aptamer samples to VEGF coated on the biacore chip. The concentration of each VEGF aptamer sample varied from 30 to 500 nM. While the Kd value of non-modified anti-VEGF 2'-OMe-RNA aptamer was $1.87 \times 10^{-9}$ M, the Kd value of PEGylated anti-VEGF 2'-OMe-RNA aptamer was $8.7 \times 10^{-8}$ M. Despite of the slightly increased Kd value after PEGylation, we could confirm the considerable binding affinity of PEGylated anti-VEGF 2'-OMe-RNA aptamer to VEGF (FIGS. 4A and 4B). Interestingly, however, there was no binding affinity for anti-VEGF DNA aptamer with the same sequence. The result indicates that the anti-VEGF DNA aptamer has no therapeutic effect despite of having the same sequence with the anti-VEGF 2'-OMe-RNA aptamer (FIG. 4C).

3.2. In Vitro Measurement of Whole Blood Clotting Time

40K PEGylated aptamer obtained by purifying with RP-HPLC in Example 2.3 was dissolved in PBS. Each 2 μL sample of PBS as a reference, unmodified anti-thrombin DNA aptamer, and PEGylated anti-thrombin DNA aptamer was mixed with 10 μL of uncoagulated whole blood obtained from health volunteers. While the samples were slowly mixed to form blood clotting, the whole blood clotting time was measured. The test was performed in duplicate.

Figure 5:
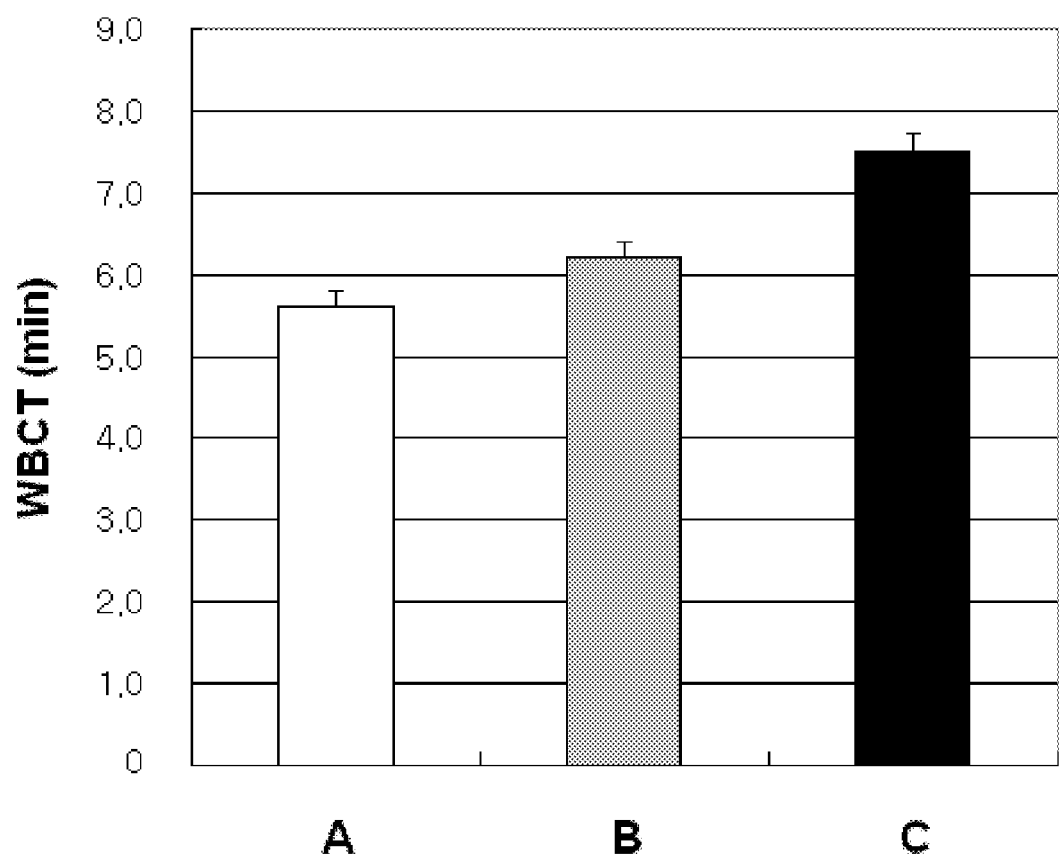
FIG. 5 is comparison of in vitro whole blood clotting times (WBCT) of (A) PBS as a reference, (B) anti-thrombin DNA aptamer and (C) PEGylated anti-thrombin DNA aptamer.
Figure 6:
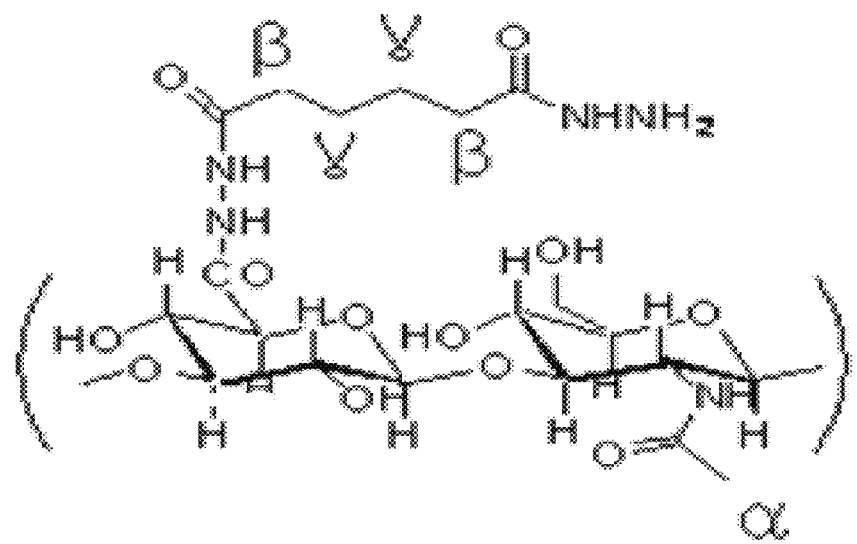
FIG. 6 is $^1$H NMR spectrum of HA-ADH which is prepared by linking adipic acid dihydrazide (ADH) to carboxyl group of HA.
Figure 6:
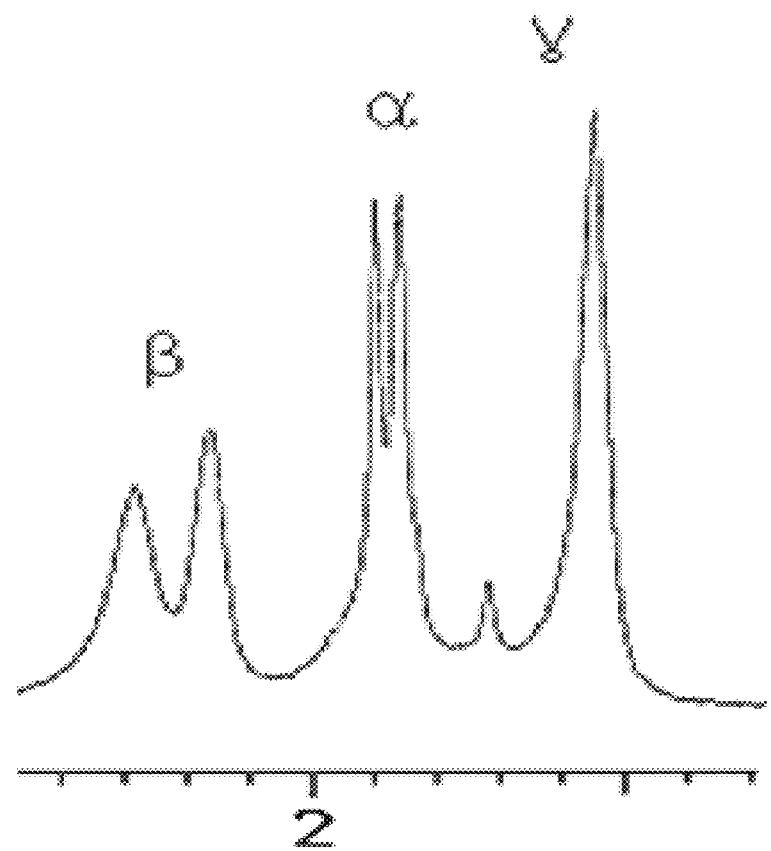

The bioactivity of PEGylated anti-thrombin DNA aptamer was assessed by measuring the whole blood clotting time (WBCT) in vitro. Previously, the half-life of anti-thrombin DNA aptamer was reported to be 108 seconds and the WBCT to be extended by 26 to 43 seconds in human plasma. PBS without aptamer was used as a control and the WBCT was about 340 seconds. The WBCT of non modified anti-thrombin DNA aptamer was 382 seconds, 42 seconds longer than that of PBS treated sample. PEGylated DNA aptamer was the longest 456 seconds reflecting its anti-thrombin bioactivity. FIG. 6 shows the WBCT of three different samples. In conclusion, the PEGylated anti-thrombin DNA aptamer appeared to have the bioactivity to retard occlusive thrombus formation in vitro. D FIG. 5 is comparison of in vitro whole blood clotting times (WBCT) of (A) PBS as a reference, (B) anti-thrombin DNA aptamer and (C) PEGylated anti-thrombin DNA aptamer.

EXAMPLE 4

Preparation of Aptamer Conjugate with HA-ADH 4.1. HA-ADH Synthesis

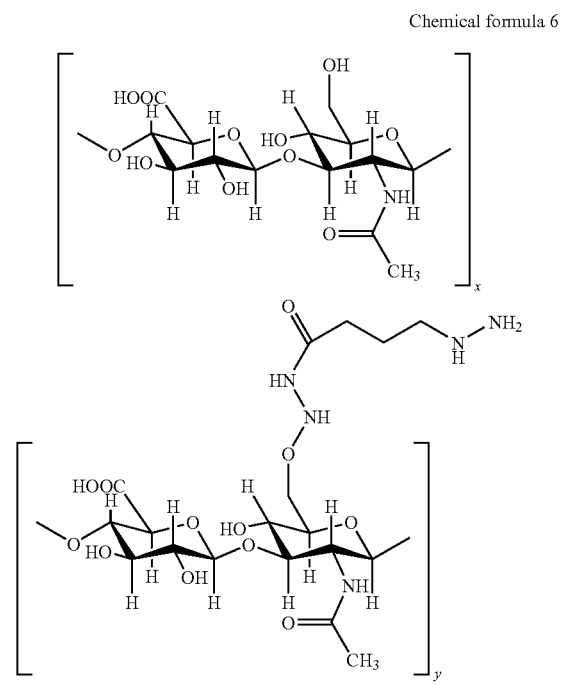

Chemical formula 6

HA with a molecular weight of 200,000 was obtained from Denkikagaku Kogyo Co. (Tokyo, Japan). Adipic acid dihydrazide (ADH) and 1-ethyl-3-[3-(dimethylamino)-propyl] carbodiimide (EDC) were purchased from Sigma-Aldrich (St. Louis, Mo., USA).

HA-ADH was prepared according to the method of Y. Luo, K. Kirker and G. D. Prestwich: J. Control. Rel. Vol. 69 (2000), p. 169. Briefly, 100 mg of HA was dissolved in 20 mL and 50 mL of water to give HA solutions of 5 mg/mL and 2 mg/mL, respectively. Forty times molar excess of solid ADH (1.736 g) was added to each solution and mixed for 10 min for complete dissolution. Then, ethanol was added and mixed for 30 min. The content of ethanol was varied by 0, 25, and 50%. The pH of the reaction mixture was adjusted to 4.8 by the addition of 1 N HCl. After that, four times molar excess of EDC (0.191 g) was added in solid form. The pH of the reaction mixture was maintained at 4.8 by the addition of 1 N HCl. After 2 hrs, the reaction was stopped by raising the pH of reaction mixture to 7.0 with 1 N NaOH. The reaction mixture was poured into the pre-washed dialysis membrane tube (MWCO of 7 kDa) and dialyzed against large excess amount of 100 mM NaCl aqueous solution, followed by dialysis against 25% ethanol and pure water. The solution was finally lyophilized for three days. The purity of HA-ADH was determined by GPC analysis, and the degree of ADH modification was measured by $^1$H NMR analysis (DPX300, Bruker, Germany).

Figure 7:
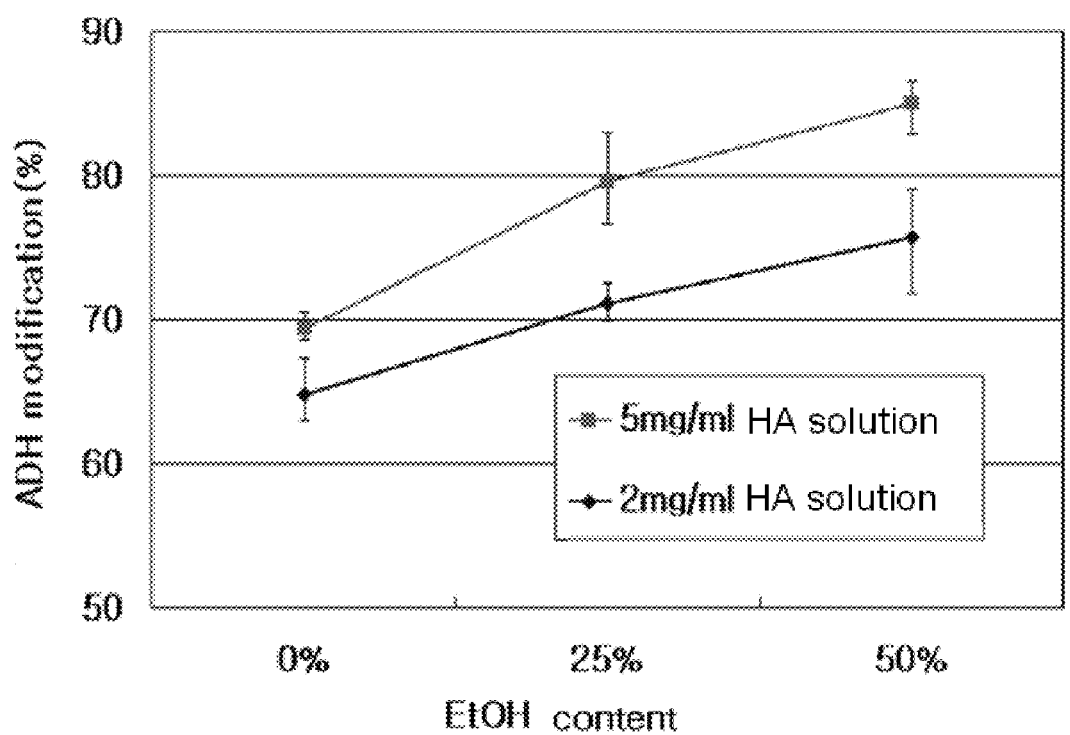
FIG. 7 is a graph showing a modification degree of ADH depending on ethanol content of reacting solvent of HA modification.

Chemical modification of HA with ADH was successfully carried out. FIG. 6 shows $^1$H NMR spectrum of HA-ADH which is prepared by linking adipic acid dihydrazide (ADH) to carboxyl group of HA. FIG. 7 is a graph showing a modification degree of ADH depending on ethanol content of reacting solvent of HA modification. FIGS. 6 and 7 show the peak assignments of HA-ADH in $^1$H NMR spectra and the degree of ADH modification determined as described elsewhere. The methyl resonance (δ=1.85-1.95 ppm) of acetamido moiety of the N-acetyl-D-glucosamine residue was used as an internal standard. The degree of ADH modification was determined by the peak areas of methylenes of ADH at δ=1.7 and 2.4 ppm. The degree of ADH modification increased up to 85 mol % with increasing ethanol content in reaction solvent. The addition of ethanol appeared to contribute for high degree of ADH modification. Therefore, as the amount of ethanol in mixed reaction solvent is higher, the long-acting activity of the aptamer increases.

4.2. Preparation of Aptamer Conjugate

Anti-thrombin DNA aptamer(5'-d(GGTTGGTGTGGT-TGG)-3' (SEQ ID NO: 1)) having a carboxyl group at 5'-terminus was activated with EDC/NHS, and reacted with HA-ADH to obtain HA-ADH-aptamer conjugate conjugate.

EXAMPLE 5

Preparation of Aptamer Conjugate with HA-TREN

HA-TREN was prepared by the substantially same method of Example 4.1 except for use of TREN instead of ADH.

To prepare HA-ADH-aptamer conjugate, anti-thrombin DNA aptamer(5'-d(GGTTGGTGTGGTTGG)-3' (SEQ ID NO:1)) was conjugated with HA-TREN instead of HA-ADH according to the substantially same method of Example 4.2.

EXAMPLE 6

Preparation of Aptamer Conjugate with HA-AEMA 6.1. HA-AEMA Synthesis

Ion exchange resin of Dowex 50WX-8-400 (25 g) was washed with water (500 mL) and filtered to remove the supernatant water three times. Then, 1.5 molar times of tetra-n-butylammonium hydroxide (TBA-OH, 48.9 mL) was added to the Dowex resin and mixed for 30 min. The filtered Dowex-TBA resin was washed with water (500 mL) three times in a same way. HA-Na (MW=200K, 5 mmol) was dissolved in 200 mL water and then the prepared Dowex-TBA (25 mmol) resin was added to the solution. After mixing for 3 hrs, the supernatant was filtered with 0.45 μm filter and then lyophilized for three days. HA-TBA was dissolved in DMSO. Then, (benzotriazol-1-yloxy) tris(dimethylamino) phosphonium hexafluorophosphate (BOP), 2-aminoethyl methacrylate hydrochloride (AEMA), and N,N-diisopropylethylamine (DIPEA) were added to the solution and mixed overnight. Finally, the reaction product was dialyzed against water and lyophilized for three days.

Figure 8:
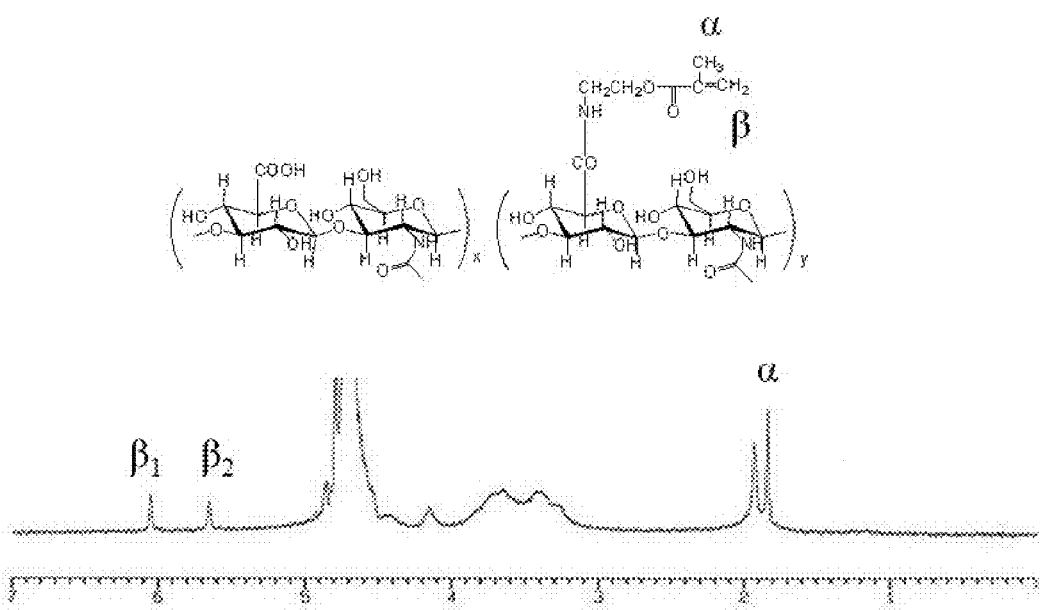
FIG. 8 is $^1$H NMR spectrum of HA-AEMA.

6.2. Preparation of Aptamer Conjugate anti-thrombin DNA aptamer(5'-d(GGTTGGTGTGGT-TGG)-3' (SEQ ID NO:1)) was dissolved in phosphate buffer (200 mM, pH8.74), and then a 10-fold molar excess of Traut's reagent (Pierce, Rockford, Ill., USA) to aptamer was dissolved in the aptamer solution. After reaction for 2 hrs, the solution was eluted through PD-10 desalting column to remove unreacted Traut's reagent. 100-fold molar excess of TCEP (Sigma-Aldrich, St. Louis, Mo., USA) to disulfide bond was dissolved in the aptamer solution and incubated for 10 min. Next, HA-AEMA (aminoethyl methacrylate) was dissolved in phosphate buffer (200 mM, pH8.74). The molar ratio of MA to aptamer was 10. After complete dissolution, the HA-AEMA solution was added to the aptamer solution, mixed immediately, and incubated at 37° C. overnight. The reaction mixture was poured into the pre-washed dialysis membrane tube (MWCO of 10 kDa) and dialyzed against large excess amount of 100 mM NaCl aqueous solution, followed by dialysis against 25% ethanol and pure water. The solution was finally lyophilized for three days. The purity of HA-aptamer conjugate was determined by GPC analysis and the extent of HA-aptamer conjugation was measured by $^1$H NMR analysis. The result shown in FIG. 8. GPC analysis was performed using the following system: Waters 1525 binary HPLC pump, Waters 2487 dual λ absorbance detector, Waters 717 plus auto-sampler, Ultrahydrogel 500 column (Milford, Mass., USA). Eluant was 34 mM phosphate buffer (pH 6.6)/methanol=80:20 (v/v) and the flow rate was 1 mL/min. Detection wavelength was 210 nm.

Figure 9:
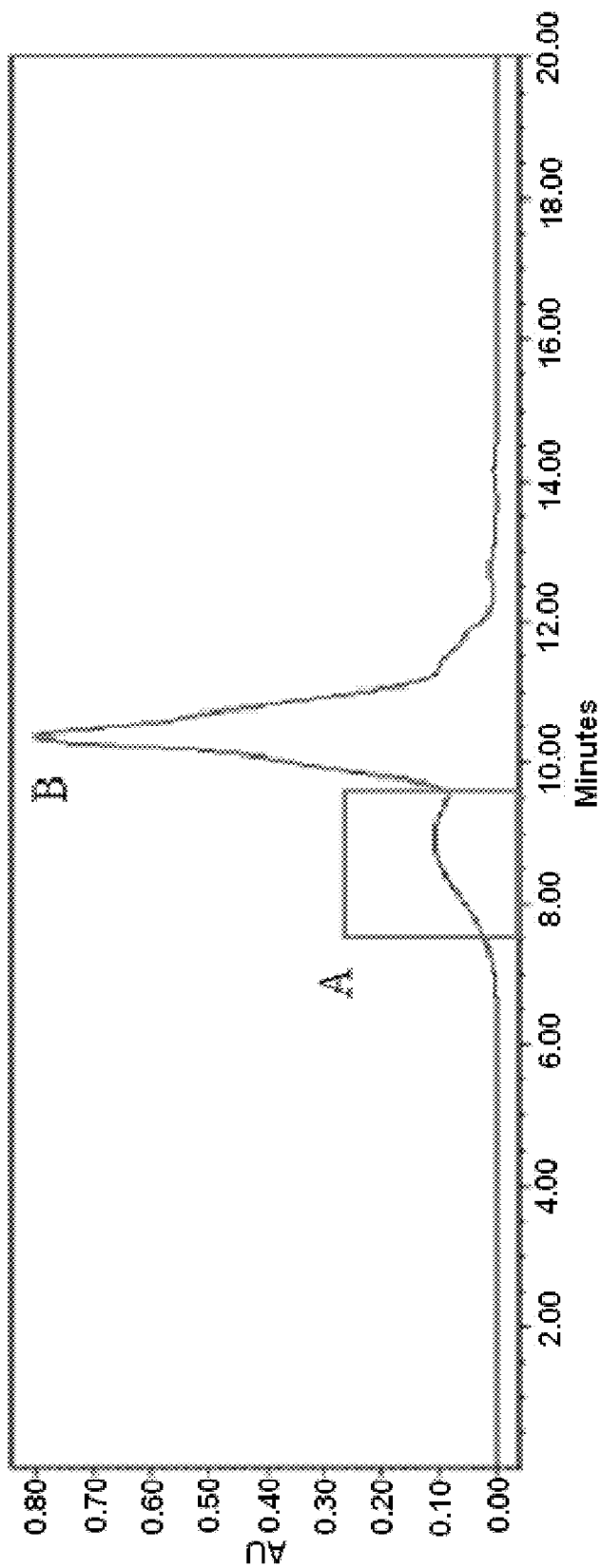
FIG. 9 is a chromatography (GPC) analysis result of HA-AEMA-aptamer conjugate which is prepared by linking HA-AEMA to aptamer containing a thiol group: A is HA-AEMA-aptamer conjugate and B is unreacted aptamer.

FIG. 9 is a chromatography (GPC) analysis result of HA-AEMA-aptamer conjugate which is prepared by linking HA-AEMA to aptamer containing a thiol group: A is HA-AEMA-aptamer conjugate and B is unreacted aptamer. In the GPC profile, the HA-aptamer conjugate peak (A) appeared earlier than the un-reacted aptamer peak (B) due to the increase of the hydrodynamic volume.

EXAMPLE 7

Preparation of Aptamer Conjugate with HA-APMAm 7.1. HA-APMAm Synthesis

HA-APMAm was prepared by the substantially same method of Example 6.1 except for use of APMAm instead of AEMA.

Figure 10:
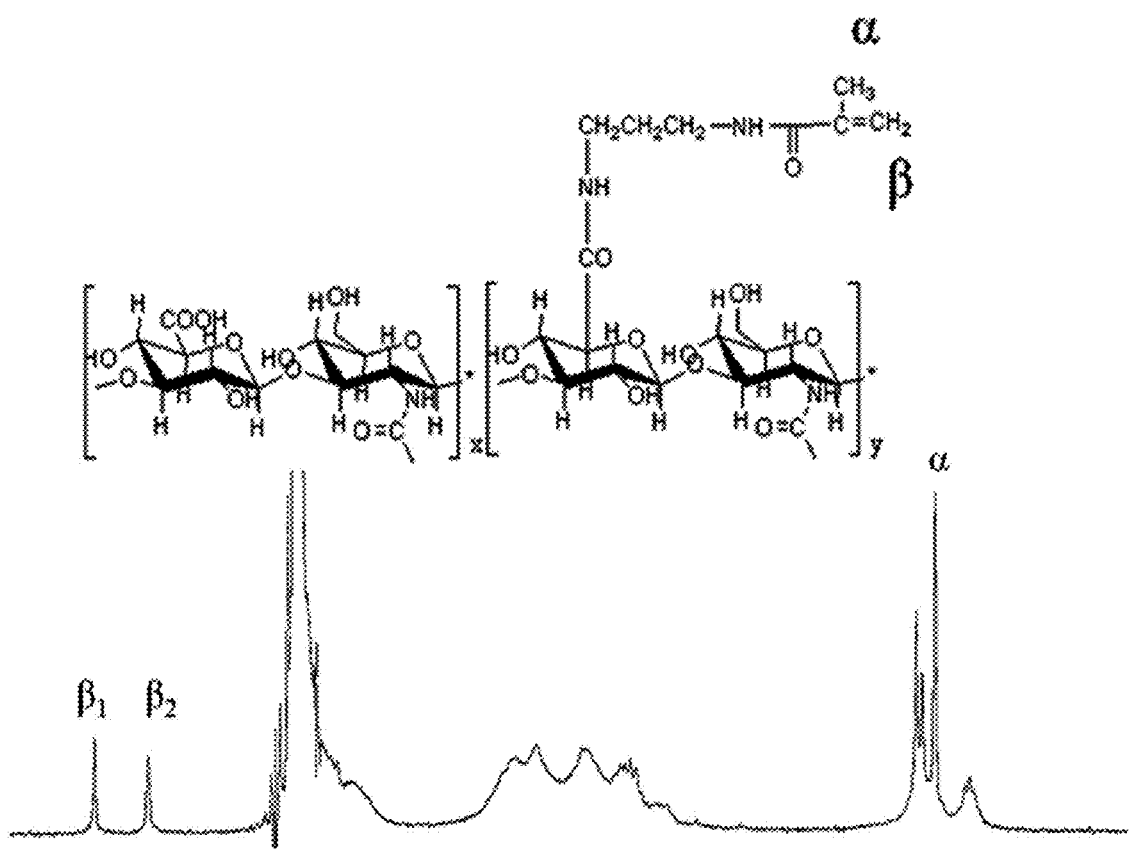
FIG. 10 is $^1$H NMR spectrum of HA-APMAm which is prepared by linking APMAm to carboxyl group of HA.

FIG. 10 shows $^1$H NMR spectrum of HA-APMAm which is prepared by linking APMAm to carboxyl group of HA. As a result of NMR analysis, substitution rate of APMAm was 55.7 mol %.

7.2. Preparation of Aptamer Conjugate

This preparation method of HA-APMAm aptamer conjugate was performed as the substantially same as that of HA-AEMA described in Example 6.2 except for use of N-(3-Aminopropyl) methacrylamide hydrochloride (APMAm) in stead of AEMA HA-AEMA.

What is claimed is:

1. A method of preparing a branch-type PEGylated aptamer comprising the steps of:

introducing two phosphoramidite derivatives at 5'-terminus of aptamer to produce a compound of chemical formula 4; and linking monomethoxy polyethylene glycol (mPEG) having a molecular weight of 10,000 to 20,000 Da to each terminal amine group of the compound of chemical formula 4 to obtain the branch-type PEGylated aptamer represented by chemical formula 5:

Chemical formula 4

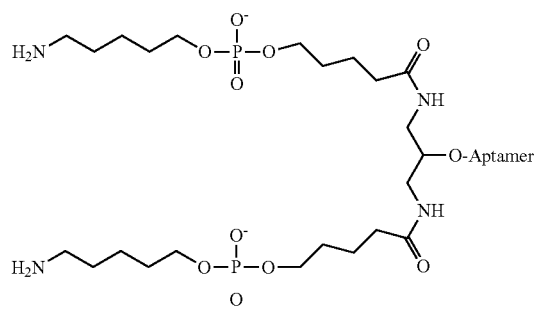

Chemical formula 5

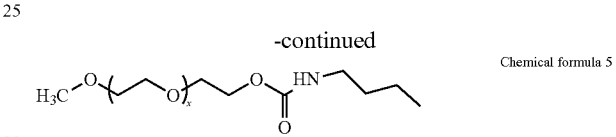

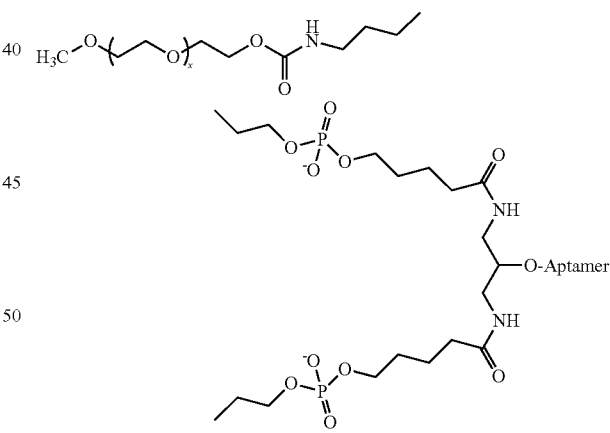

In chemical formula 5, x is an integer of 170 to 350.

2. The method of preparing a branch-type PEGylated aptamer according to claim 1, wherein the method is performed by coupling symmetric doubler phosphoramidite to 5'-terminus of an oligonucleotide aptamer synthesized using solid phase polymerization, introducing a terminal amine group of the linked doubler phosphoramidite, and combining the PEG with the terminal amine group.

* * * * *